United States Patent
Ogawa

(10) Patent No.: US 6,647,792 B2
(45) Date of Patent: *Nov. 18, 2003

(54) ULTRASONIC PROBE, ULTRASONIC RECEIVER AND ULTRASONIC DIAGNOSTIC APPARATUS

(75) Inventor: Eiji Ogawa, Minami-Ashigara (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/844,074

(22) Filed: Apr. 30, 2001

(65) Prior Publication Data

US 2001/0042410 A1 Nov. 22, 2001

(30) Foreign Application Priority Data

May 2, 2000 (JP) .................................. 2000-133085
Feb. 2, 2001 (JP) .................................. 2001-026293

(51) Int. Cl.[7] ........................................... G01N 25/00
(52) U.S. Cl. ........................... 73/656; 73/601; 73/608; 73/655
(58) Field of Search ........................... 73/608, 601, 620, 73/635, 643, 655, 656, 657; 356/352, 358; 600/445, 447

(56) References Cited

U.S. PATENT DOCUMENTS

| | | | | |
|---|---|---|---|---|
| 3,831,135 A | * | 8/1974 | Smith ........................... | 73/608 |
| 4,006,627 A | * | 2/1977 | Bossaert ....................... | 73/608 |
| 4,554,836 A | * | 11/1985 | Rudd ........................... | 73/655 |
| 4,873,989 A | * | 10/1989 | Einzig ......................... | 73/801.52 |
| 5,080,491 A | * | 1/1992 | Monchalin et al. .......... | 356/352 |
| 5,103,676 A | * | 4/1992 | Garcia et al. ................. | 73/597 |
| 5,305,756 A | * | 4/1994 | Entrekin et al. ............. | 600/445 |
| 5,353,262 A | * | 10/1994 | Yakymshyn et al. .......... | 73/655 |
| 5,419,329 A | * | 5/1995 | Smith et al. ................. | 600/447 |
| 5,450,752 A | * | 9/1995 | White et al. ................. | 73/643 |
| 5,457,997 A | * | 10/1995 | Naruo et al. ................. | 73/643 |
| 5,814,730 A | * | 9/1998 | Brodeur et al. .............. | 73/597 |
| H1813 H | * | 11/1999 | Kersey ........................ | 372/94 |

OTHER PUBLICATIONS

E.D. Light et al "Progress in Two–Dimensional Arrays for Real–Time Volumetric Imaging UltrasonicImaging" 20, 1–15 (1998).

Takahashi et al, "Underwater Acoustic Sensor With Fiber Bragg Grating Optical Review", vol. 4, No. 6 (1997) 6911–694.

Uno et al, Fabrication and Performance of a Fiber Optic Micro–Probe for Megahertz Ultrasonic Field Measurement T. IEEE Japan, vol. 118–E, NO. 11, 1998.

* cited by examiner

Primary Examiner—Hezron Williams
Assistant Examiner—Jacques Saint Surin
(74) Attorney, Agent, or Firm—Sughrue Mion, PLLC

(57) ABSTRACT

An ultrasonic probe which does not require electric wiring to a large number of microcomponents and does not induce increase of crosstalk and electric impedance. This ultrasonic probe comprises an optical transmission path array incorporating a plurality of optical transmission paths on which light is incident at first ends thereof; and a plurality of ultrasonic detecting elements which are formed on these optical transmission at the second ends thereof and adapted to reflect the light incident through the respective fibers based on ultrasonic waves applied thereon.

36 Claims, 19 Drawing Sheets

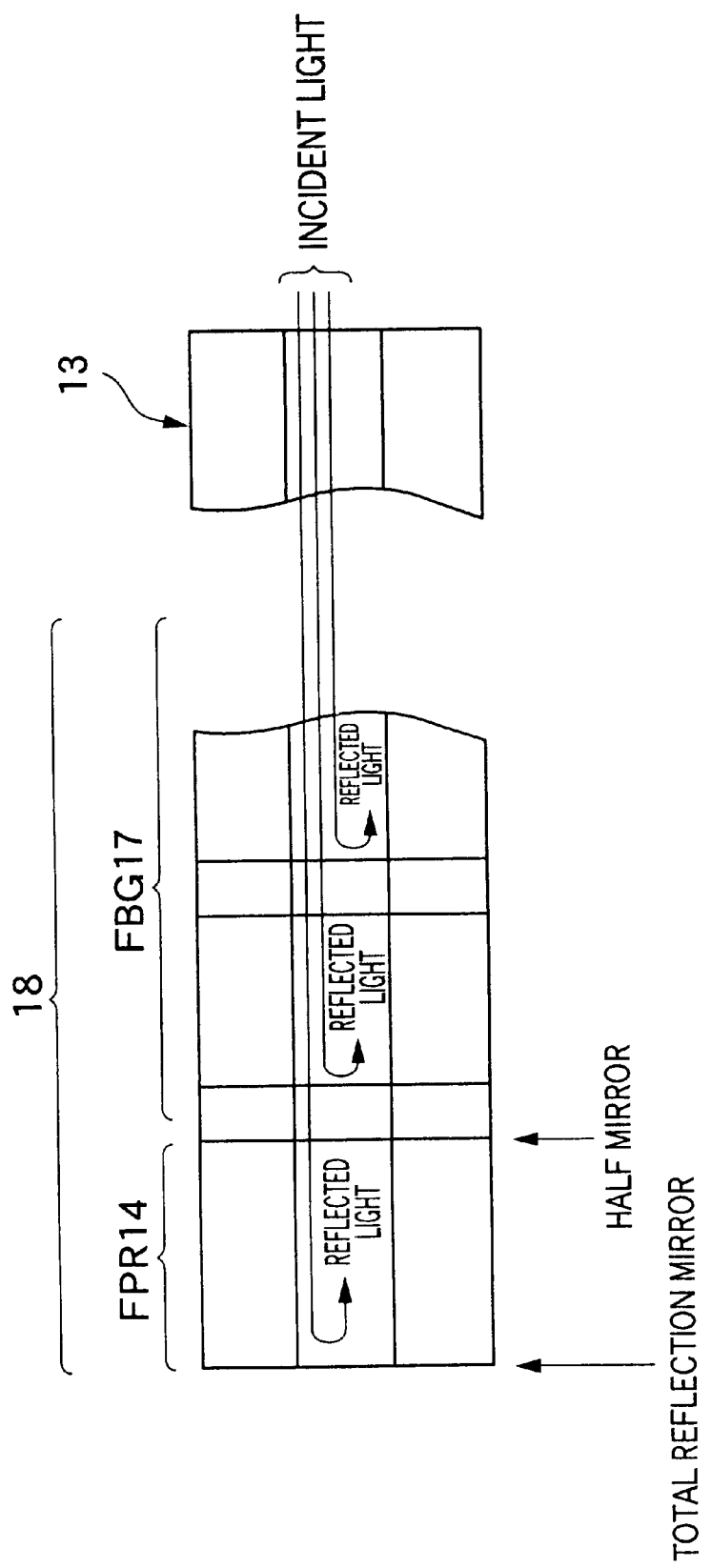

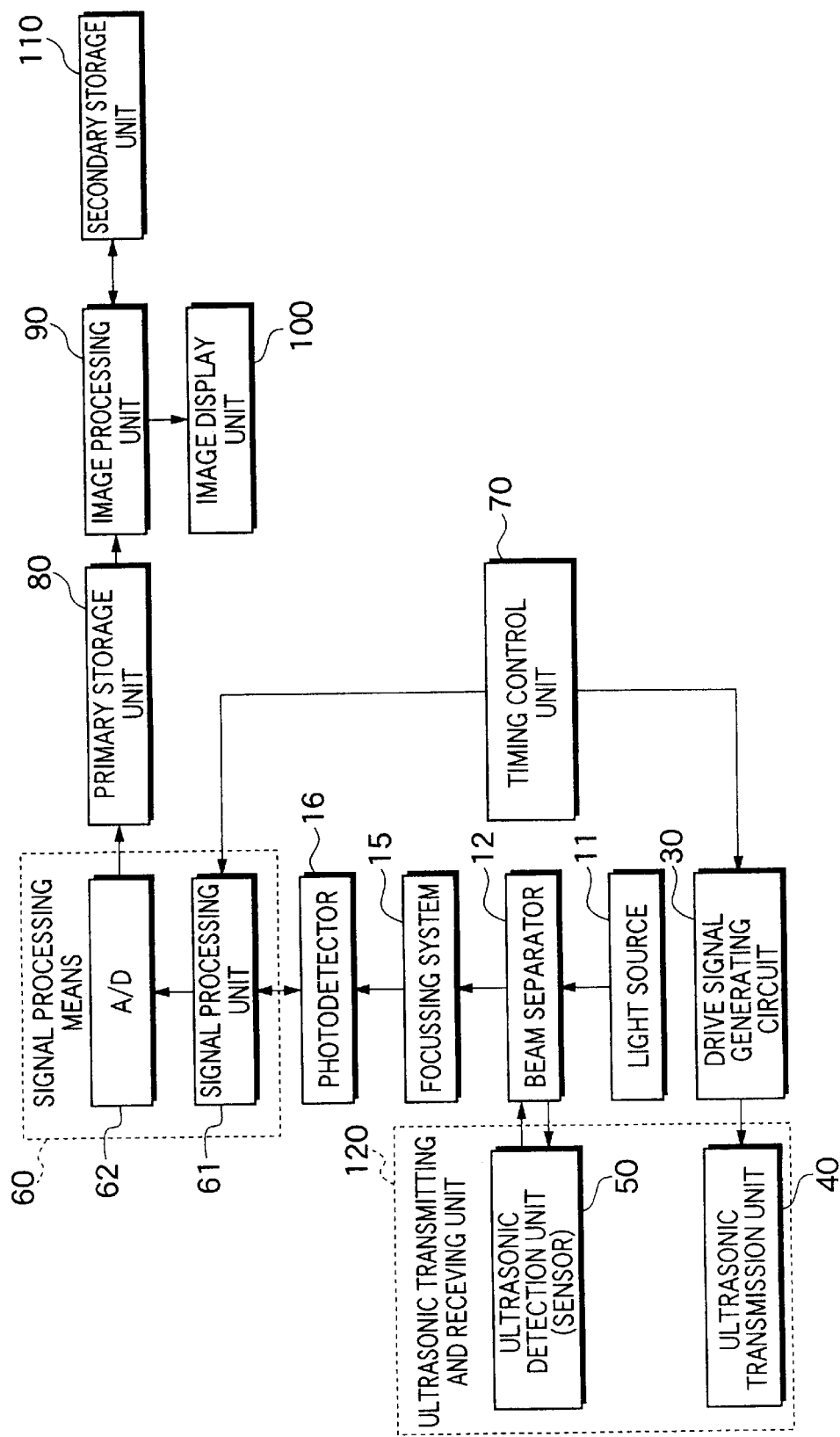

ULTRASONIC PROBE, ULTRASONIC RECEIVER AND ULTRASONIC DIAGNOSTIC APPARATUS

BACKGROUND OF THE INVENTION

1. Field of the Invention

The present invention relates to an ultrasonic probe, an ultrasonic receiver, and an ultrasonic diagnostic apparatus for performing medical diagnosis by receiving ultrasonic waves through the use of the foregoing ultrasonic probe and ultrasonic receiver.

2. Description of a Related Art

Conventionally, when acquiring a three-dimensional image through the use of ultrasonic waves, a plurality of two-dimensional images of sections in a direction of depth have been obtained and synthesized. These two-dimensional images can be obtained by scanning a one-dimensional sensor array fitted with a position sensor, and further a three-dimensional image can be obtained by synthesizing the plurality of two-dimensional images which were obtained in time series.

In this technique, however, a time lag exists in a scanning direction of the one-dimensional sensor array and therefore the sectional images generated at different times are synthesized, whereby the resultant synthetic image becomes out of focus. Accordingly, such approach is not suitable for imaging of an object like a living body which is accompanying some movement.

In order to obtain a three-dimensional image in real time, it is essential to provide a two-dimensional sensor array which can obtain a two-dimensional image without putting a sensor array into scanning operation, and there is thus a need of developing such a sensor array.

In an ultrasonic diagnostic apparatus, piezoelectric ceramics represented by PZT (Pb (lead) zirconate titanate) and polymer piezoelectric elements such as PVDF (polyvinyl difluoride) piezoelectric polymer are typically used as an element (oscillator or probe) for transmitting and/or receiving ultrasonic waves, and a technique for fabricating a two-dimensional array incorporating these elements is now under examination. However, using the PZT or PVDF as mentioned above requires microfabrication of the elements and wiring to a large number of microcomponents, and it is difficult to increase the fineness and integration of the elements beyond those possible in the present state. Even if these difficulties are solved, however, there remain such problems that crosstalk between the elements increases, and that a rise in electrical impedance caused by such fine wiring deteriorates a signal-to-noise ratio and increases the susceptibility of a microcomponent at an electrode part to fracture, which makes the implementation of such a two-dimensional sensor array using PZT or PVDF difficult.

For example, ULTRASONIC IMAGING 20, 1–15 (1998) carries a paper entitled "Progress in Two-Dimensional Arrays for Real-Time Volumetric Imaging" by E. D. LIGHT et al., Duke University. This paper discloses a probe comprising a two-dimensional array of PZT ultrasonic sensors. This paper, however, concurrently describes as follows: "To make similar quality images, two dimensional array would require 128×128=16,384 elements. Because of the cost and complexity of building such a large number of RF channels, it is unlikely that anyone will construct such an ultrasonic imaging system in the near future. Also, connecting to so many elements in such a dense aperture is very difficult. (page 2, lines 14–18)."

On the other hand, a sensor incorporating an optical fiber has been applied to an ultrasonic sensor without the use of any piezoelectric materials such as PZT. As such optical fiber ultrasonic sensors, there have been reported those incorporating a fiber Bragg grating (abbreviated as FBG) (see the paper Takahashi et al., Japan Defense Academy, "Underwater Acoustic Sensor with Fiber Bragg Grating", OPTICAL REVIEW Vol. 4, No. 6 (1997) pp. 691–694) and those incorporating a Fabry-Perot resonator (abbreviated as FPR) structure (see the paper Uno et. al., Tokyo Institute of Technology "Fabrication and Performance of a Fiber Optic Micro-Probe for Megahertz Ultrasonic Field Measurements" T. IEE Japan, Vol. 118-E, NO.11, '98), all of which are discrete sensors, and the idea of forming a sensor array composed of such sensors has not been reported.

Also, the above-mentioned document written by TAKAHASHI et al. describes that these sensors may have certain sensitivities with respect to such ultrasonic waves having relatively low frequency ranges, e.g., on the order of 20 kHz. However, no description is made as to such ultrasonic waves operable in megahertz-order frequency ranges which are used in the actual ultrasonic diagnoses. As a consequence, in order to practically use these sensors, sensor operations with respect to ultrasonic waves having higher frequency ranges than those of the described examples are necessarily confirmed. Furthermore, conditions should be researched, if required, under which better sensor sensitivities could be obtained in such high frequency ranges.

SUMMARY OF THE INVENTION

The present invention is provided in view of the aforementioned problems. The first object of the present invention is to provide an ultrasonic probe comprising a sensor array which does not require electric wiring to a large number of microcomponents and does not induce increase of crosstalk and electric impedance. The second object of the present invention is to provide an ultrasonic receiver which can obtain a three-dimensional image data without scanning the probe. Further, the third object of the present invention is to provide an ultrasonic diagnostic apparatus using such an ultrasonic probe and ultrasonic receiver.

To solve the problems mentioned above, an ultrasonic probe according to the present invention comprises: an optical transmission path array including a plurality of optical transmission paths on which light is incident at first ends thereof; and a plurality of ultrasonic detecting elements, formed at second ends of the plurality of optical fibers and modulate the light coming through the respective optical fibers depending on an applied ultrasonic wave.

Further, an ultrasonic receiver according to the present invention comprises: a plurality of ultrasonic detecting elements which are arranged in the form of two-dimensional array and modulate light depending on an applied ultrasonic wave; and a photodetector for detecting light emerging from the plurality of ultrasonic detecting elements.

Still further, an ultrasonic diagnostic apparatus in according to the present invention comprises: a drive signal generating circuit for generating a drive signal to transmit ultrasonic waves; an ultrasonic transmission unit for transmitting ultrasonic waves to an object in response to the drive signal supplied from the drive signal generating circuit; an ultrasonic detection unit including a plurality ultrasonic detecting elements for selectively reflecting light, each of said plurality of ultrasonic detecting elements for modulating light depending on ultrasonic waves applied thereto; a photodetector for detecting the light output from the ultrasonic detection unit to generate a detection signal; signal processing means for processing the detection signal supplied from the photodetector; and control means for controlling transmission timing of the drive signal generating circuit and receive timing of the signal processing means.

According to the present invention light is used for detecting ultrasonic waves, and therefore, there is no need for electric wiring to a large number of microcomponents and crosstalk and increase in electric impedance are not caused. Thus, an ultrasonic probe and ultrasonic receiver both of which are easy to manufacture and provide a good SN ratio, and an ultrasonic diagnostic apparatus using them can be implemented.

BRIEF DESCRIPTION OF THE DRAWINGS

FIG. 15 is a diagram schematically showing a part of an ultrasonic receiver according to a seventh embodiment of the present invention;

FIG. 22 is a block diagram showing an ultrasonic diagnostic apparatus according to a second embodiment of the present invention.

DESCRIPTION OF THE PREFERRED EMBODIMENTS

In the following, the present invention will be detailed with reference to the accompanying drawings, wherein identical or similar components are designated by the same reference numbers and descriptions thereof are omitted.

Figure 1:
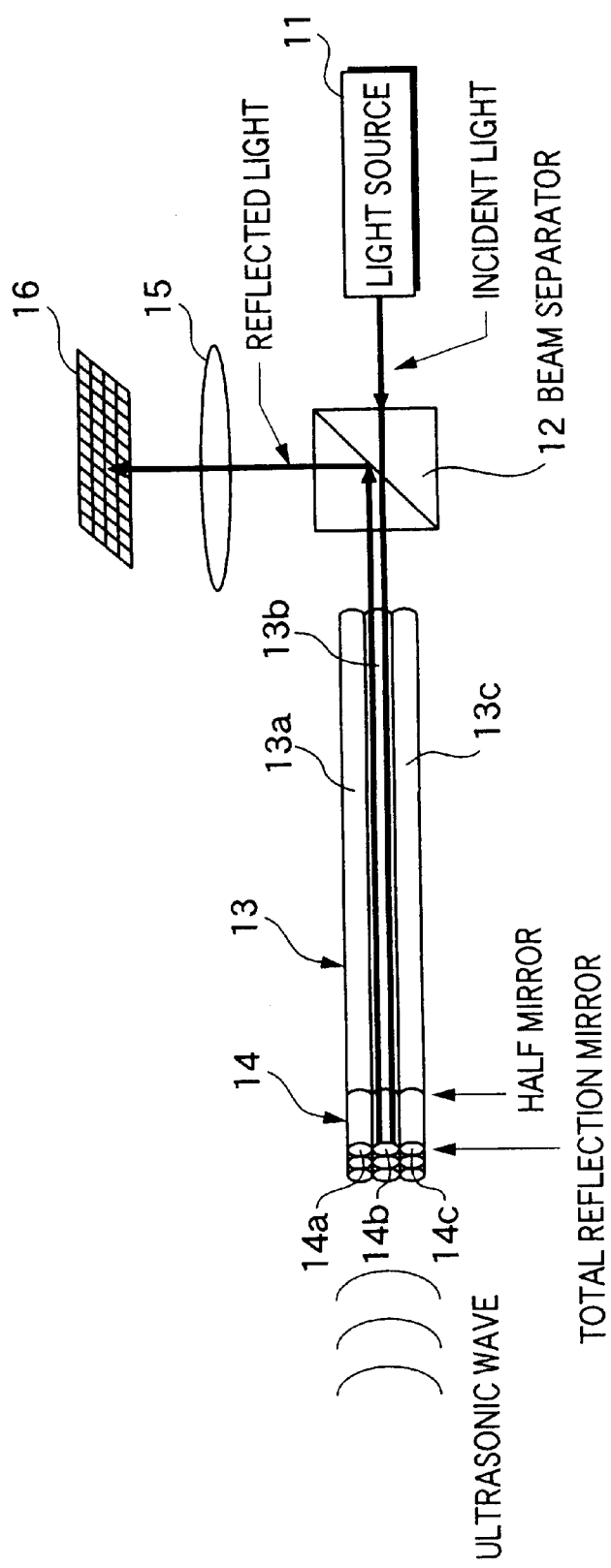
FIG. 1 is a diagram schematically showing an ultrasonic receiver according to first embodiment of the present invention.

FIG. 1 is a diagram schematically showing an ultrasonic receiver according to a first embodiment of the present invention.

This ultrasonic receiver comprises a light source 11 for generating single mode laser light having a single wavelength preferably in a range of 500 nm to 1600 nm. The light generated by the light source 11 enters a beam separator 12 which is constructed using a half mirror, an optical circulator, a polarizing beam splitter, or the like. The beam separator 12 transmits the incident light from a first direction toward a second direction, and transmits the reflected light returned from the second direction toward a third direction which is different from the first direction. In the present invention, a half mirror is used as the beam separator 12. The half mirror transmits the incident light and redirects the reflected light returned from the direction opposite to the incident direction in a direction at about 90 degrees with respect to the incident direction.

The light emitted from the light source 11 and transmitted through the beam separator 12 is then directed onto an optical fiber array 13. The optical fiber array 13 includes fine optical fibers 13a, 13b, . . . which are arrayed in the form of a two-dimensional arrangement. It is desirable that these optical fibers are single mode fibers. In addition, a single light source may be provided and assigned to a plurality of optical fibers or a plurality of light sources may be provided and assigned to a plurality of light fibers. Further, the light generated by a single light source may be directed onto the plurality of optical fibers with scanning the light in time series.

The optical fiber array 13 has ultrasonic detecting elements 14 in the tip thereof. The ultrasonic detecting elements 14 are Fabry-Perot resonators (abbreviated as FPR) 14a, 14b, . . . formed in the tips of the optical fibers 13a, 13b, . . . respectively.

Each FPR has a half mirror formed at one end thereof (the right in the drawing) and a total reflection mirror formed at the other end thereof (the left in the drawing), and the light incident upon the ultrasonic detecting elements 14 are partially or totally reflected by these mirrors. The total reflecting surface undergoes geometrical displacement by ultrasonic waves applied to the ultrasonic detecting elements 14, thereby the reflected light is modulated and directed onto the beam separator 12 again. The reflected light entering the beam separator 12 is subjected to the change of the traveling path and directed onto a photodetector 16 comprising a CCD, a photodiode (PD) array, or the like. Here, the reflected light may be incident upon the photodetector 16 directly or via the optical fibers or the like, or the reflected light may be focussed on the photodetector 16 via a focussing system 15 such as a lens by disposing the focussing system downstream of the beam separator 12.

Next, operations of the Fabry-Perot resonator composing the ultrasonic detecting element 14 are described in greater detail. The Fabry-Perot resonator comprises a half mirror prepared by gold evaporation or the like on the tip of the single mode optical fiber, a cavity composed by members including polyester resin or the like which is disposed at the end successively from the half mirror, and a total reflection mirror which is formed by gold evaporation or the like and disposed at the end successively from the cavity. The members composing the cavity experience a geometrical displacement due to the application of the ultrasonic waves thereto.

Detection light having a wavelength λ is launched into this Fabry-Perot resonator from the half mirror side, and ultrasonic waves are applied from the total reflection mirror. Assuming that the length of cavity is L and the refractive index is n, the reflection property $G_R$ of the Fabry-Perot resonator is represented by the following equation:

$$G_R = \frac{(\sqrt{R} - G_S)^2 + 4\sqrt{R}\,G_S \sin^2(2\pi n L/\lambda)}{(1 - \sqrt{R}\,G_S)^2 + 4\sqrt{R}\,G_S \sin^2(2\pi n L/\lambda)} \quad (1)$$

Where R is the reflectance of the half mirror, and Gs is the gain of the single path. With this equation, it can be seen that the intensity of the light reflected from the Fabry-Perot resonator is altered as the optical path length L of the cavity changes owing to the alteration of the sound pressure of the ultrasonic waves.

The reflection property of the Fabry-Perot resonator is characterized by a gradient band of the reflectance varies considerably between the wavelength which maximizes the reflectance and the wavelength which minimizes the reflectance, where the reflectance changes significantly. Fluctuation of the intensity of the reflected light can be observed by applying ultrasonic waves to the Fabry-Perot resonator with permitting the light having a wavelength within the gradient band to enter the Fabry-Perot resonator. The ultrasonic intensity can be measured by converting this fluctuation of the light intensity. This Fabry-Perot resonator is short in sensor length, and thus features a resolving power in the axial direction of the sensor.

Figure 2:
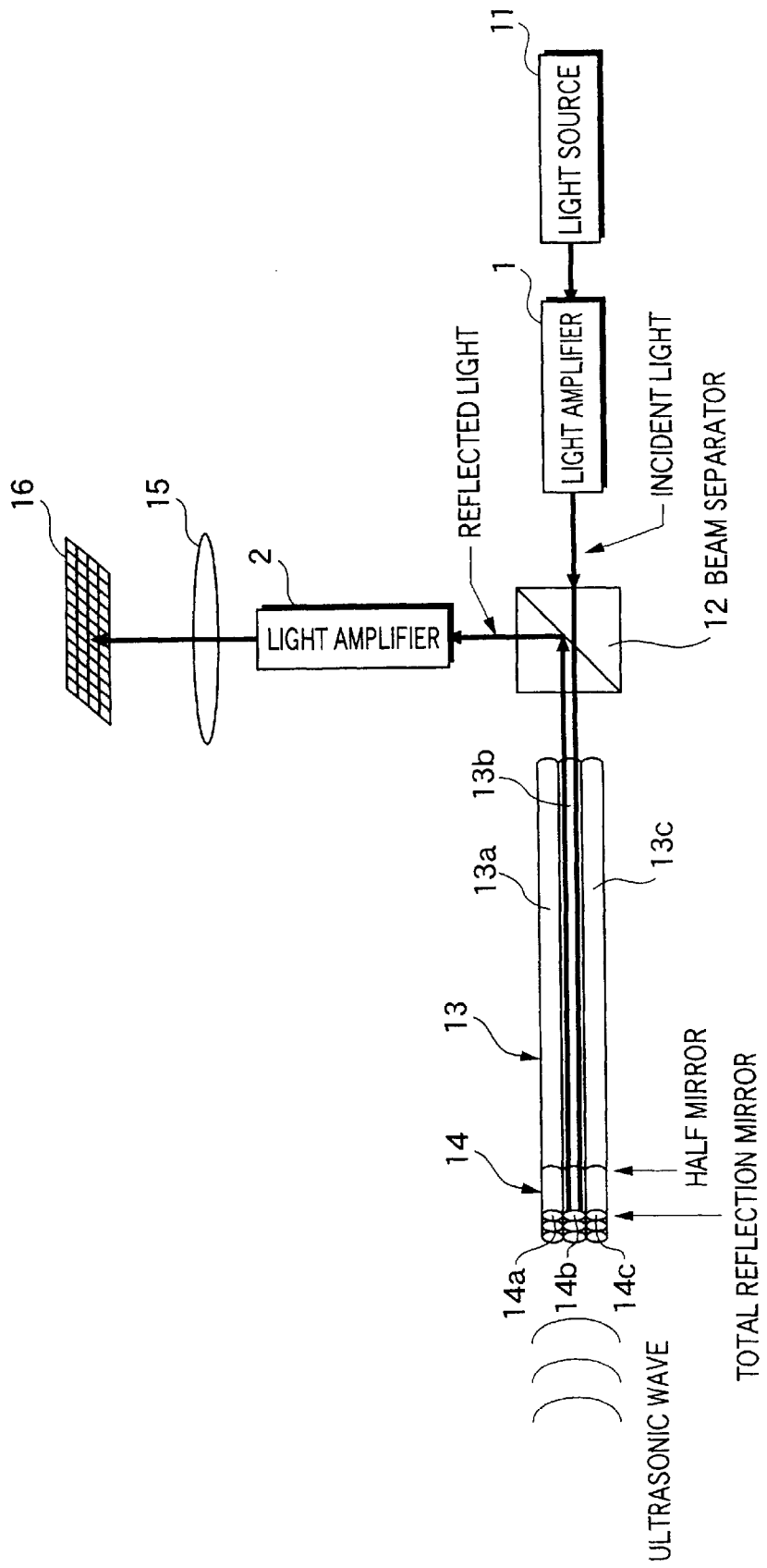
FIG. 2 is a diagram schematically showing an ultrasonic receiver according to a second embodiment of the present invention.

Next, a second embodiment of the present invention will be described below. FIG. 2 is a diagram schematically showing an ultrasonic receiver according to the second embodiment of the present invention.

This ultrasonic receiver is modified from that of the first embodiment shown in FIG. 1 by adding at least one of optical amplifiers 1 and 2. The optical amplifier 1 is positioned between the light source 11 and the beam separator 12 and serves to amplify the light incident from the light source 11 and emit the amplified light toward the beam separator 12. On the other hand, the optical amplifier 2 is positioned between the beam separator 12 and the focussing system 15 such as a lens and serves to amplify the light incident from the beam separator 12 and emit the amplified light toward the focussing system 15. If the focussing system 15 is not used, the optical amplifier 2 is positioned between the beam separator 12 and the photodetector 16, and serves to amplify the light incident from the beam separator 12 and emit the amplified light toward the photodetector 16.

As the optical amplifier, a optical fiber amplifier doped with Erbium as known by EDFA (Er—Doped Optical Fiber Amplifier) is used by way of example. This EDFA is able to boost the light intensity from ten to one hundred fold.

When such an optical amplifier is positioned between the light source 11 and the optical fiber array 13, the intensity of the light incident upon the ultrasonic detecting elements 14 is enhanced. On the other hand, when the optical amplifier is positioned between the optical fiber array 13 and the photodetector 16, the intensity of the light incident upon the ultrasonic detecting elements 14 does not change, but the intensity of the reflected light incident on the photodetector 16 is enhanced. In this case, the intensity fluctuation of the reflected light modulated by the received ultrasonic waves is enhanced as well.

In either case, the light quantity of the reflected light incident upon the photodetector 16 is increased by boosting the intensity in a light state, which allows to effectively reduce the effect on the photodetector 16 of the electric noises and improve the SN ratio of the ultrasonic receiver. Further, the combined use of them allows the further improvement of the SN ratio.

Figure 3:
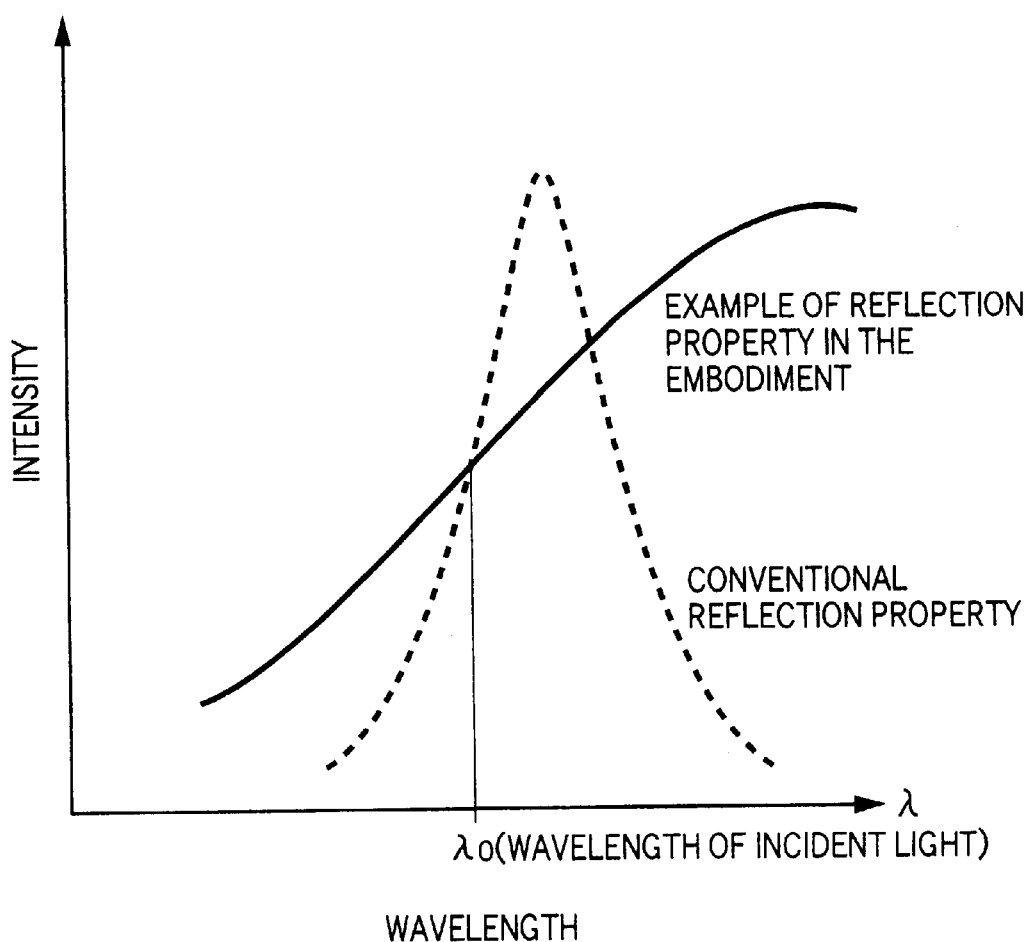
FIG. 3 is a diagram showing an example of reflection property of an ultrasonic detecting element incorporated in the ultrasonic receiver according to the second embodiment of the present invention.

Still further, with the configuration of this embodiment, the SN ratio at the ultrasonic receiver is improved. Such improvement may be reflected to ease the specification requirements on the filter property. For example, as shown in FIG. 3, the inclination of the reflection property 14 may be made gentle. In this case, the manufacture of the ultrasonic detecting elements 14 is facilitated. Further, since a linear section of the reflection property is extended, ultrasonic waves can be detected accurately even if the wavelength $\lambda_0$ of the incident light fluctuates in some extend depending on the temperature.

Figure 4:
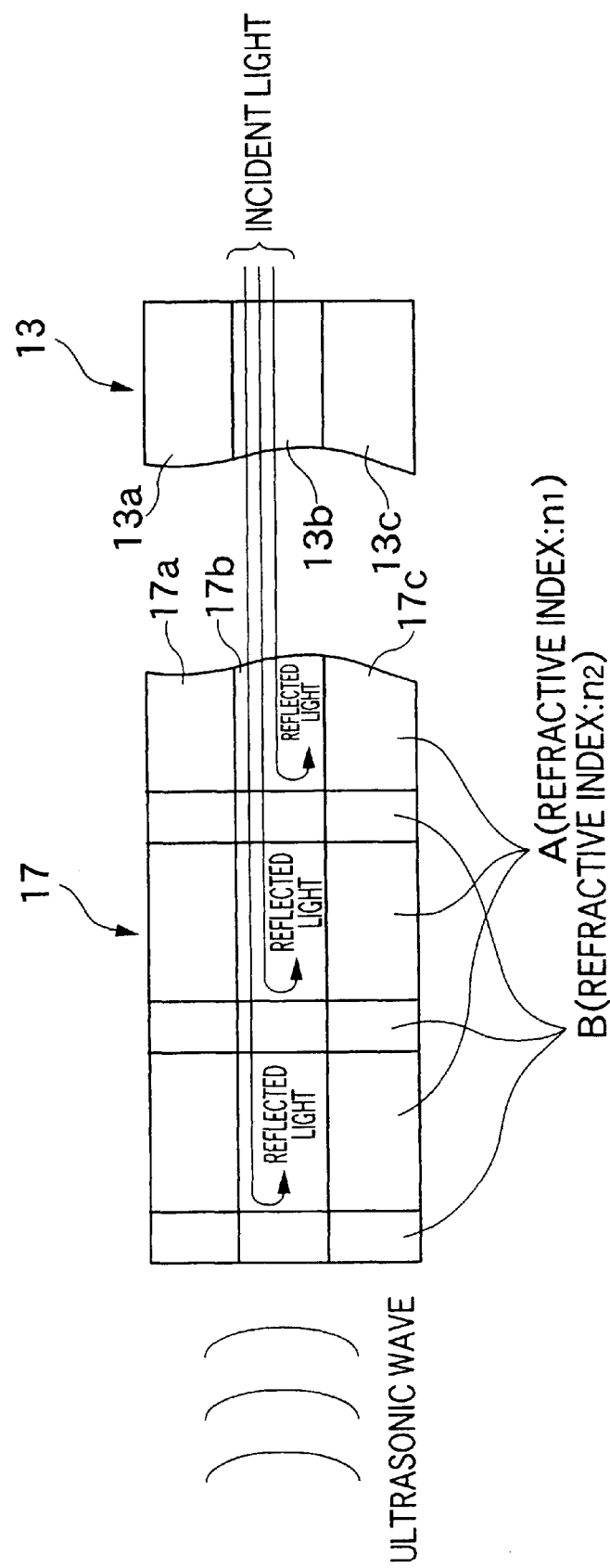
FIG. 4 is a diagram schematically showing a part of an ultrasonic receiver according to a third embodiment of the present invention.

Next, an ultrasonic receiver according to a third embodiment of the present invention will be described below. FIG. 4 is a diagram schematically showing a part of an ultrasonic receiver according to the third embodiment of the present invention. This ultrasonic receiver employs fiber Bragg grating (abbreviated as FBG) instead of the Fabry-Perot resonator in the first embodiment. That is, in the third embodiment, ultrasonic detecting elements 17 using the Bragg grating construction are provided on the tip of the optical fiber array 13 which is same as that shown in FIG. 1. The ultrasonic detecting elements 17 are composed of Bragg grating portions 17a, 17b, . . . which are formed on the tips of the optical fibers 13a, 13b, . . . respectively.

The Bragg grating portion is a multilayered stack formed by alternating some thousands of layers including two kinds of materials (light propagation medium) different in refractive index to be layered at a certain pith so as to satisfy the Bragg reflection condition. The FBG has higher reflectance and more abrupt wavelength dependence than those of the single layer Fabry-Perot resonator. A material layer "A" having a refractive index $n_1$ and a material layer "B" having a refractive index $n_2$ are shown in FIG. 4. Assuming the pitch (spacing) of the periodic structure of these layers as d, and the wavelength of the incident light as λ, the Bragg reflection condition is represented by equation (2), provide that m is any integer.

$$2d \cdot \sin\theta = m\lambda \quad (2)$$

where θ is an incident angle from the plane of incidence. Rewriting the equation by letting θ=π/2, equation (3) is given as follows:

$$2d = m\lambda \tag{3}$$

The Bragg grating portion selectively reflects the light having a specific wavelength which satisfies the Bragg reflection condition, while allowing the transmission of all the light having other wavelengths.

When the ultrasonic waves are allowed to propagate into the Bragg grating portion, the Bragg grating portion is distorted so as to change the pitch "d" of the periodic structure mentioned above, whereby the wavelength λ of the selectively reflected light varies. The reflection property of the Bragg grating portion is characterized by a gradient band located before and after the central wavelength of the highest reflectance (with low transmittance) within which the reflectance varies. A detection light having a central wavelength within the range of the gradient band is launched into the Bragg grating portion while applying thereto the ultrasonic waves. Thus the intensity fluctuation of the reflected light (or transmitted light) depending of the intensity of the ultrasonic waves can be observed. The ultrasonic intensity can be measured by converting this fluctuation of the light intensity. This fiber Bragg grating has a good sensitivity and is readily produced. Consumer fiber Bragg gratings may be diverted for this purpose.

In this case, generally speaking, Bragg gratings may be easily manufactured while having high sensitivities, and therefore, commercially available Bragg grating products may be alternatively employed. However, these commercially available Bragg grating products cannot be directly used as high sensitive sensors in ultrasonic diagnostic purposes. For example, when a Brag grating used in this market is employed, such a confirmation can be made. That is, in a frequency band higher than 20 kHz, a sensitivity of this Bragg grating with respect to ultrasonic waves entered along an axial direction would be lowered. Also, in the case that a length of an ultrasonic sensing part (Bragg grating portion) is longer than approximately ¾ of a wavelength of an ultrasonic wave entered to the Bragg grating portion, a detected waveform is distorted on the side of the low frequency band, as compared with the waveform of the actually received ultrasonic wave, and the sensor sensitivity is lowered. This ultrasonic wavelength is expressed as follows:

(ultrasonic wavelength)=(sound velocity in Bragg grating portion)/(frequency of ultrasonic wave).

These waveform distortion and lowering of sensor sensitivity may be conceived by the following reasons: In such a case that the length of the Bragg grating portion is longer than a half of the ultrasonic wave wavelength in the Bragg grating portion, while the ultrasonic wave is propagated through the Bragg grating portion, such a portion that expand/compress phases are inverted is produced in the Bragg grating portion. As a result, displacement of these portions is canceled.

To avoid an occurrence of such a phenomenon, a length of a Bragg grating portion may be selected to be shorter than, or equal to approximately ¾ of an ultrasonic wavelength, preferably to be equal to an approximately half of this ultrasonic wavelength. For instance, in such a case that a frequency of an ultrasonic wave to be detected is selected to be 3.5 MHz, and a sound velocity within a material of a Bragg grating portion is equal to 5,500 m/s, a wavelength "$\lambda_s$" of an ultrasonic wave which is propagated through the Bragg grating portion may be calculated as follows:

$\lambda_s = 5500/(3.5 \times 10^6) = 1571.4$ (micrometers)

As a result, an upper limit length of the Bragg grating portion may be calculated as follows:

$1571 \times (¾) = 1178.5$ (micrometers)

As a result, if a length of such a Bragg grating portion is shorter than, or equal to 1178.5 micrometers, then it is possible to prevent inversion of expand/compress phases occurred in the Bragg grating portion, and also possible to obtain sensitivities required to detect ultrasonic waves.

Figure 5:
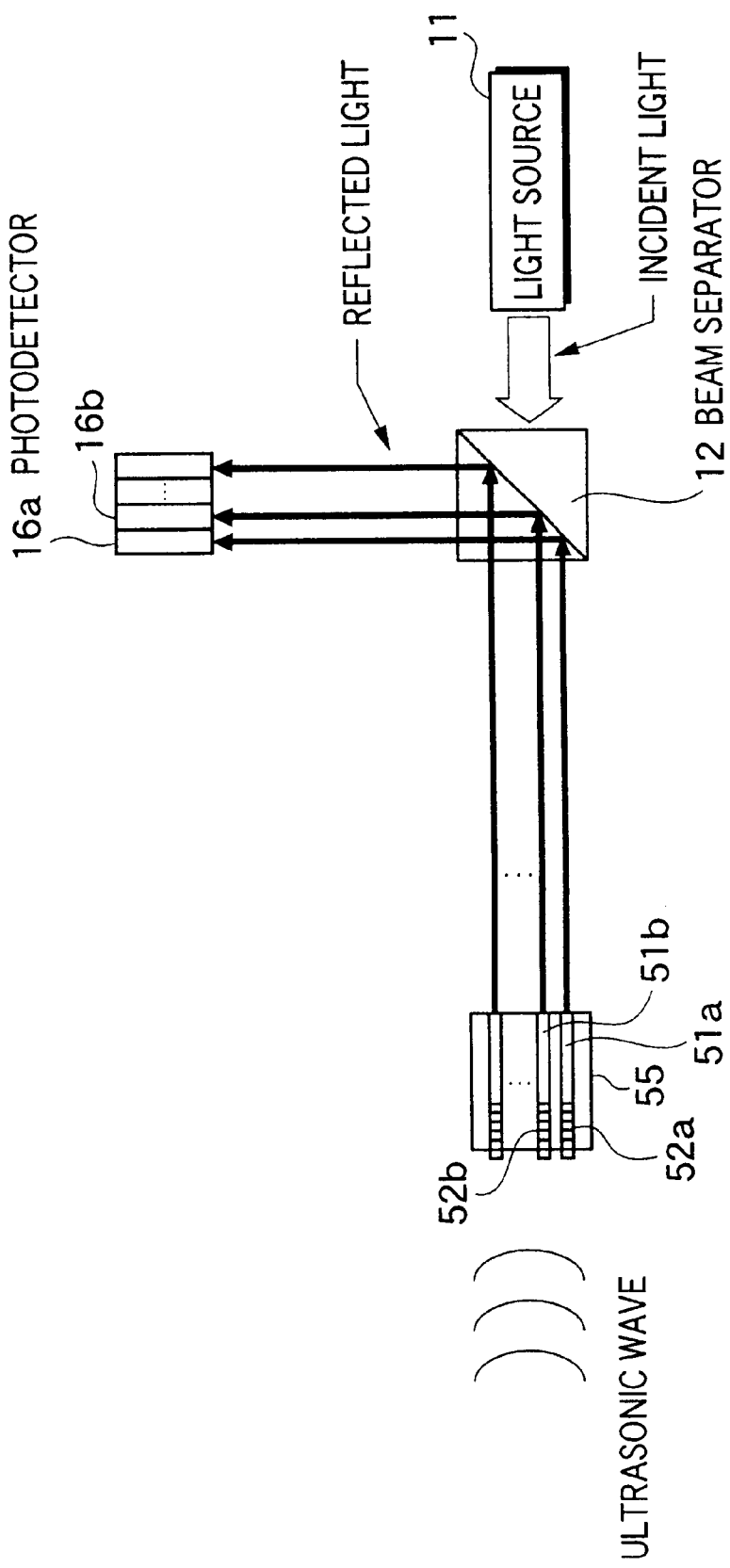
FIG. 5 is a diagram schematically showing an ultrasonic receiver according to a fourth embodiment of the present invention.

Next, an ultrasonic receiving apparatus according to a fourth embodiment of the present invention will now be described with reference to FIG. 5. This fourth embodiment is featured by that an optical waveguide path having a Bragg grating structure is employed as an ultrasonic wave detecting element. FIG. 5 illustratively shows a basic idea of an arrangement of the ultrasonic receiving apparatus according to this fourth embodiment. As indicated in FIG. 5, a plurality of optical waveguide paths 51a, 51b, . . . are formed on a substrate 55. Further, Bragg grating portions 52a, 52b, . . . are formed on core tip portions of these optical waveguide paths, respectively. Light emitted from a light source 11 passes through a beam separator (optical demultiplexer) 12 and then the separated light is entered into the respective optical waveguide paths 51a, 51b, . . . . In each of the respective optical waveguide paths, the Bragg grating portion formed at the tip portion thereof is changed in the structural aspect due to the propagation of the ultrasonic wave, so that the light is modulated. In each of the optical waveguide paths, the travel path of the light which is reflected by the Bragg grating portion is changed in the beam separator 12, and then the reflected light is entered into photodetectors 16a, 16b, . . . corresponding to the respective optical waveguide paths 51a, 51b, . . . . As explained above, since changes in light intensity are detected by the photodetectors 16a, 16b, . . . strengths of ultrasonic waves which are propagated through the corresponding optical waveguide paths can be measured. It should be understood that similar to the third embodiment, in this fourth embodiment, a length of a Bragg grating portion formed on an optical waveguide path is preferably made shorter than, or equal to ¾ of a wavelength of an ultrasonic wave propagated through this Bragg grating portion.

Figure 7:
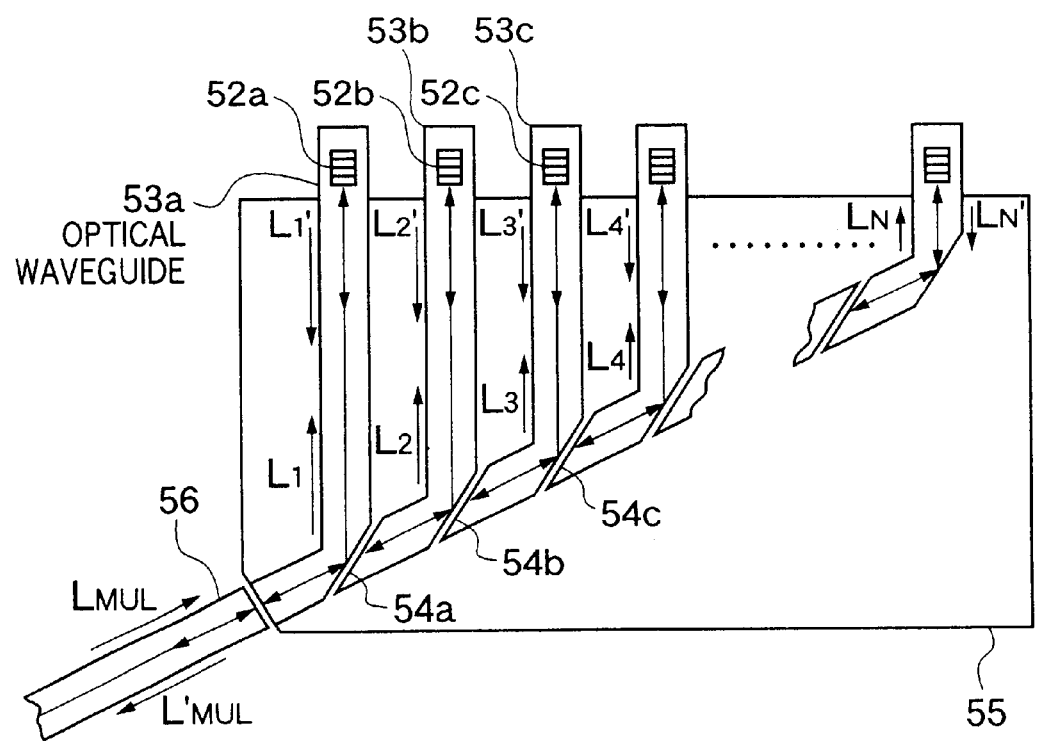
FIG. 7 is a diagram showing construction of an ultrasonic detection unit as shown in FIG. 6.
Figure 8:
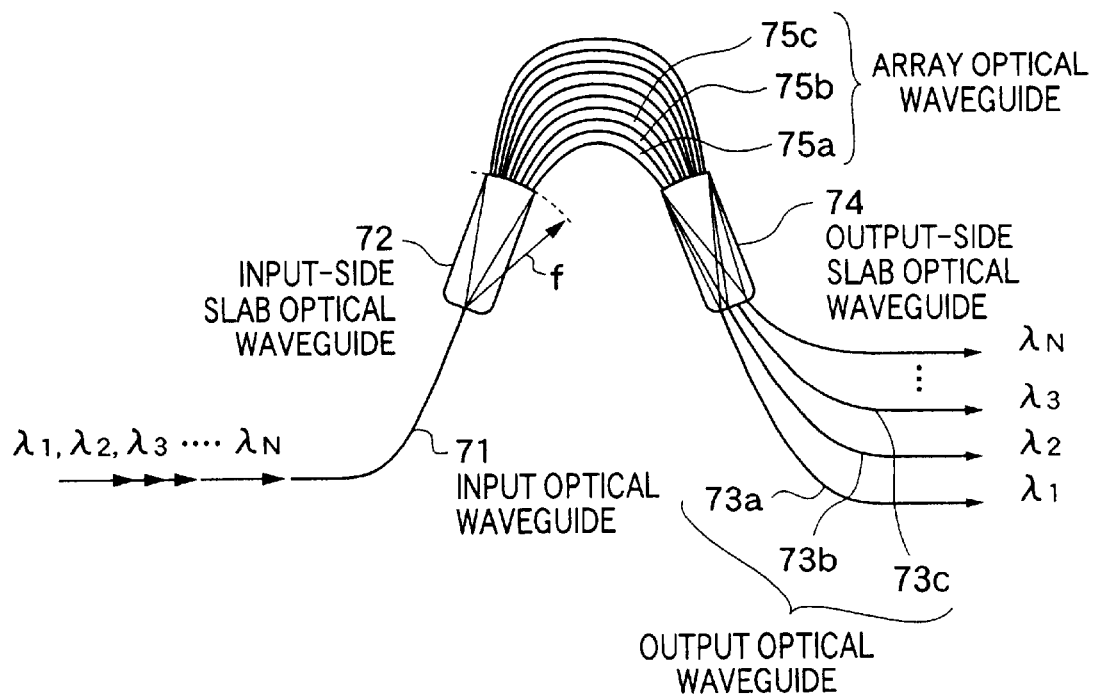
FIG. 8 is a diagram showing construction of a beam separator as shown in FIG. 6.

Next, an ultrasonic receiving apparatus according to a fifth embodiment of the present invention will now be explained with reference to FIG. 6 to FIG. 8. This fourth embodiment is featured by that while an optical waveguide path 53 having a Bragg grating structure is employed as an ultrasonic detecting element, a plurality of light having different wavelengths is multiplexed with each other, and then, the multiplexed light is used as detection light. FIG. 7 illustratively shows a basic idea of an arrangement of the ultrasonic receiving apparatus according to this fifth embodiment. FIG. 7 illustratively indicates a structure of an ultrasonic detecting unit 50 shown in FIG. 6. FIG. 8 illustratively represents a structure of a beam separator 41 shown in FIG. 6.

Figure 6:
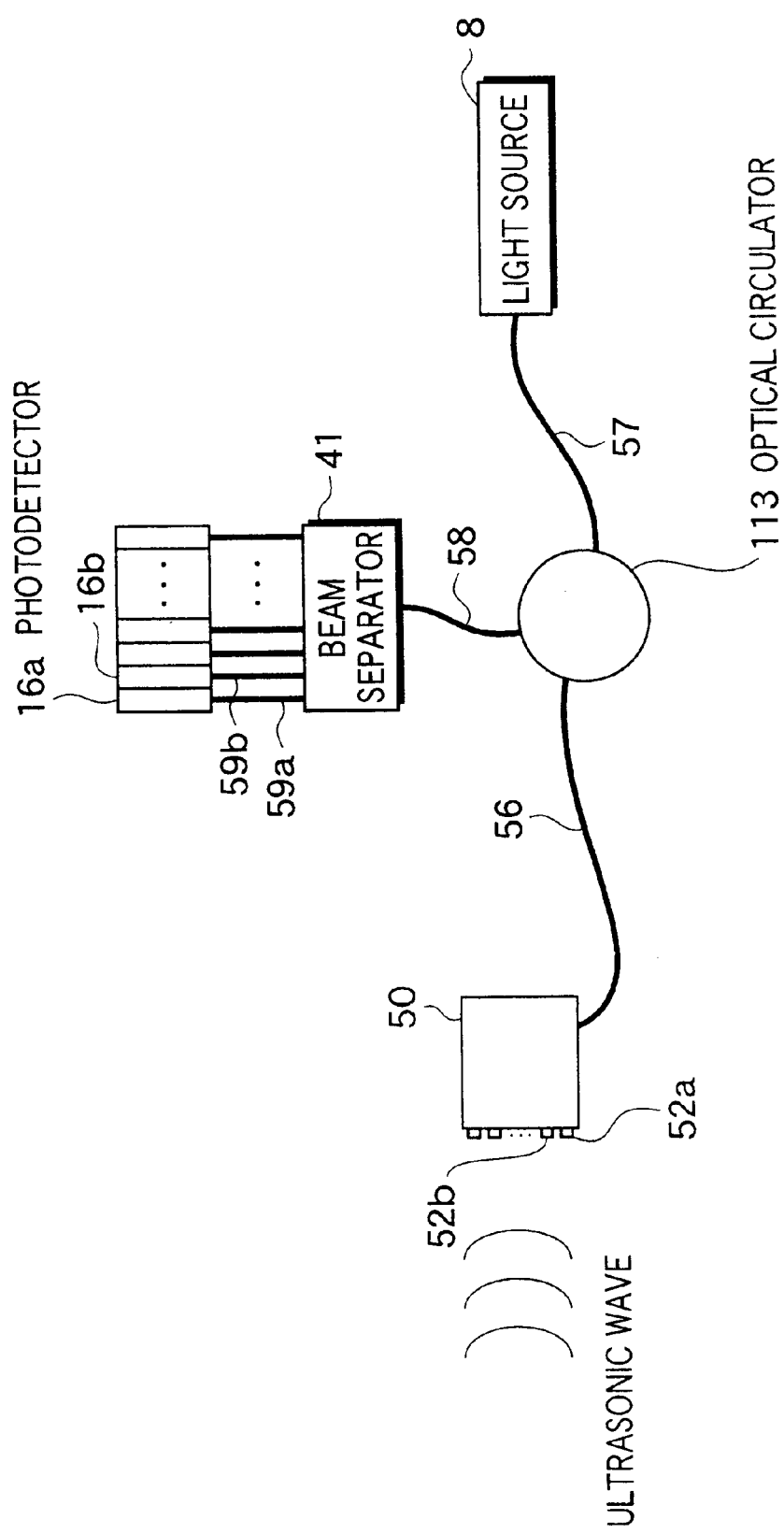
FIG. 6 is a diagram schematically showing an ultrasonic receiver according to a fifth embodiment of the present invention.

As shown in FIG. 6, this ultrasonic receiving apparatus includes a light source 8, an optical circulator 113, an ultrasonic detecting unit 50, a beam separator (optical demultiplexer) 41, photodetectors 16a, 16b, . . . and optical fibers 56, 57, 58, 59a, 59b, . . . . The ultrasonic detecting unit 50 includes an optical waveguide path having a Bragg grating structure. The beam separator 41 separates detecting light which is entered from the ultrasonic detecting unit 50. The photodetectors 16a, 16b, . . . detect intensity of separated light. The optical fibers 56, 57, 58, 59a, 59b, . . . connect these units to each other. In this fourth embodiment, as the light source 8, a broad-band light source is used for producing light having a broad band (broad-band light). As the beam separator, an optical circulator 113 is used for switching a propagation direction of light in response to a light incident direction.

In FIG. 6, the light emitted from the light source 8 is entered via the optical fiber 57 into the optical circulator (spectrometer) 12, and further is entered via the optical fiber 56 to the ultrasonic detecting unit 50.

Referring now to FIG. 7, the ultrasonic detecting unit 50 contains a plurality of optical waveguide paths 53a, 53b, . . . formed on the substrate 55. These optical waveguide paths 53a, 53b, . . . own inverted "L" shapes and also different waveguide paths from each other. These light waveguide paths 53a, 53b, . . . are arranged in such a manner that sections thereof are arranged along one column. The Bragg gratings 52a, 52b, . . . are formed on the tip portions of the respective optical waveguide paths 23a, 23b, . . . .

In this fourth embodiment, a pitch of a periodic structure of each layer which constitutes each of the Bragg gratings is determined based upon the formula (3) in such a manner that a reflection wavelength characteristic is increased with respect to a specific wavelength. In other words, the pitch "d" of the periodic structure of each layer which constitutes the Bragg grating 52a is determined based upon the formula (3) in such a manner that the Bragg wavelength becomes "$\lambda_1$". Also, the pitch "d" of the periodic structure of each layer which constitutes the Bragg grating 52b is determined based upon the formula (3) in such a manner that the Bragg wavelength becomes $\lambda_2$ (being not equal to $\lambda_1$). This pitch determining method may be similarly applied to the remaining Bragg gratings 52c, 52d, . . . . As a consequence, the reflection wavelength characteristics of the Bragg gratings 52a, 52b, . . . are different from each other. When ultrasonic waves are applied to a plurality of Bragg gratings 52a, 52b, . . . these Bragg gratings are compressed along the sound pressure direction of the ultrasonic waves. As a result, the pitches "d" of the periodic structures of the respective layers which constitute the respective Bragg gratings 52a, 52b, . . . are changed, so that the respective Bragg wavelengths are varied. As a consequence, while the ultrasonic waves are received, the light which is entered into the respective Bragg gratings 52a, 52b, . . . is modulated in response to the applied ultrasonic waves. It should also be noted that in this fourth embodiment, the lengths of the Bragg grating portions formed at the tip portions of the respective optical waveguide paths may be preferably selected to be shorter than, or equal to ¾ of the wavelength of the ultrasonic wave, similar to the third embodiment.

A tail portion of the optical waveguide path 52a is connected to the optical fiber 56. Also, a gap 54a is formed between the tail portion of the optical waveguide path 53a and a tail portion of the optical waveguide path 53b. This gap 54a may function as a beam splitter. Similarly, another gap 54b functioning as a beam splitter is formed between the tail portion of the optical waveguide path 53b and a trail portion of the optical waveguide path 53c. This gap formation is similarly applied to the remaining optical waveguide paths 53c, 53d, . . . . In this fourth embodiment, a plurality of optical waveguide paths 53a, 53b, . . . are connected in such a manner, so that a planar lightwave circuit (PLC) may be realized.

In this case, operations of the ultrasonic detecting unit 50 indicated in FIG. 7 will now be explained. When light $L_{MUL}$ containing a plurality of wavelength components ($\lambda_1, \lambda_2, \ldots \lambda_N$) are supplied to this ultrasonic detecting unit 50, this light is demultiplexed every this light passes through a plurality of gaps 54a, 54b, . . . respectively. The light $L_1$ (having wavelength of $\lambda_1$) entered into the optical waveguide path 53a is reflected by the Bragg grating 52a toward the optical waveguide path 53a, and is modulated in response to the ultrasonic wave applied to this Bragg grating 52a to thereby produce light $L_1'$. The light $L_2$ (having wavelength of $\lambda_2$) entered into the optical waveguide path 53b is reflected by the Bragg grating 52b toward the optical waveguide path 53b, and is modulated in response to the ultrasonic wave applied to this Bragg grating 52b to thereby produce light "$L_2'$." The above-described light process operation is similarly applied to the remaining light $L_3$ (having wavelength of $\lambda_3$), light $L_4$ (having wavelength of $\lambda_4$), . . . contained in the light $L_{MUL}$. The projection light $L_1', L_2', \ldots$ of the Bragg gratings 52a, 52b, . . . is sequentially multiplexed with each other in the corresponding gaps 54a, 54b, . . . and then, the multiplexed light is entered into the optical fiber 56.

Referring again to FIG. 6, the travel direction of light entered into the optical fiber 56 is changed by the optical circulator 113, and then, this light is entered via the optical fiber 58 to the demultiplexer (beam separator) 41. The beam separator 41 demultiplexes the light $L_{MUL}'$ entered from the optical fiber 58 to produce a plurality of light $L_1', L_2', \ldots$ having predetermined wavelengths different from each other. A plurality of photodetectors 16a, 16b, . . . having the different detectable wavelength ranges are connected via the corresponding optical fibers 59a, 59b, . . . to the beam separator 41. Since a plurality of photodetectors 16a, 16b, . . . detect the light $L_1', L_2', \ldots$ which is entered from the corresponding optical fibers 59a, 59b, . . . it is possible to detect the strengths of the ultrasonic waves applied to the respective Bragg gratings 52a, 52b, . . . which are contained in the ultrasonic detecting unit 50.

Referring now to FIG. 8, in this sixth embodiment, as the demultiplexer, a demultiplexing circuit is employed which contains an arranged-wavelength grating (AWG) corresponding to one sort of the planar lightwave circuit (PLC). This multiplexing circuit is arranged in such a manner that a plurality of array optical waveguides 75a, 75b, . . . having a constant waveguide path difference are connected between an input-sided slab optical waveguide path 72 to which one input optical waveguide path 71 is connected, and also an output-sided slab optical waveguide path 74 to which a plurality of output optical waveguide paths 73a, 73b, . . . .

The input-sided slab optical waveguide path 72 has a fan shape, while an end portion of the input optical waveguide path 71 is located as a center of a curvature, whereas the output-sided slab optical waveguide path 74 has a fan shape, while end portions of the plural output optical waveguide paths 73a 73b, . . . are located as a center of a curvature. A plurality of array optical waveguide paths 75a, 75b, . . . are arranged in a radial shape in such a way that the respective optical axes thereof may pass through both the curvature centers of the input-sided slab optical waveguide path 72 and the output-sided slab optical waveguide path 74. As a result, both the input-sided slab optical waveguide path 72 and the output-sided slab optical waveguide path 74 may realize such operations equivalent to a lens.

In the case that the light $L_{MUL}'$ containing a plurality of wavelength components ($\lambda_1, \lambda_2, \ldots \lambda_N$) is entered into the input optical waveguide path 71, this light is extended in the input-sided slab optical waveguide path 72 due to diffraction so as to excite a plurality of array optical waveguide paths 75a, 75b, . . . with in-phase condition. When the respective excitation light passes through the corresponding array optical waveguide paths 75a, 75b, . . . phase differences corresponding to the optical waveguide path differences are given to the excitation light, and thereafter the excitation light is reached to the output-sided slab optical waveguide path 74. When a plurality of light entered into the output-sided slab optical waveguide path 74 will interfere with each other because of the lens effect, the interfering light is focused onto one point on the side where a plurality of output optical waveguide paths 73a, 73b, . . . and then is diffracted in such a direction along which the in-phase condition can be satisfied. It should also be understood that in the demultiplexing circuit (beam separator) shown in FIG. 8, if the units provided on the input side are replaced by the units provided on the output side, then this demultiplexing circuit may be employed as an optical multiplexing circuit.

In this sixth embodiment, the broad-band light source has been used as the light source. Alternatively, while a plurality of laser oscillators having different wavelengths are employed, laser light emitted from these laser oscillators is multiplexed with each other to produce multiplexed laser light. Then, this multiplexed laser light may be employed as the light source. In this alternative case, the demultiplexer (beam separator) as shown in FIG. 8 may be employed as the multiplexer.

Figure 9:
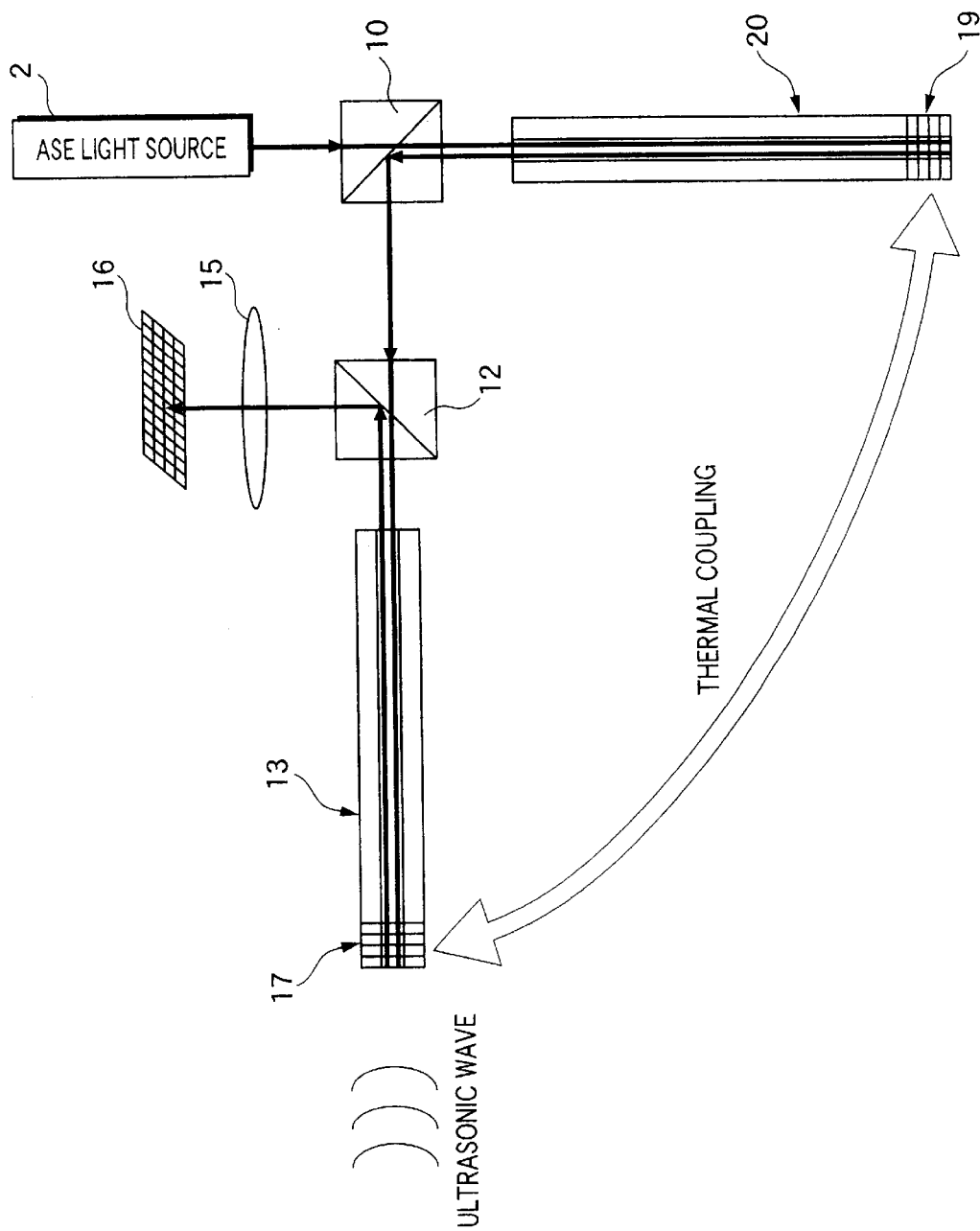
FIG. 9 is a diagram schematically showing an ultrasonic receiver according to a sixth embodiment of the present invention.

Next, an ultrasonic receiver according to a sixth embodiment of the present invention will be described below. FIG. 9 shows a diagram schematically showing an ultrasonic receiver according to the present embodiment. The ultrasonic receiver according to the present embodiment is modified from that of the first to fifth embodiments by changing the light source in order to use the light emitted from a broadband light source by narrowing the transmission band thereof with a narrow-band-pass filter.

As the broadband light source, an ASE (Amplified Spontaneous Emission) light source 9, from which the amplified spontaneous emission light is emitted, is used by way of example. The ASE light source 9 is modified from a broadband optical fiber amplifier by changing the structure thereof so as to be able to emit amplified spontaneous emission light. For more information on the broadband optical fiber amplifier, see, for example, Haruki Ohgoshi "Broadband Optical Fiber Amplifier" (Review of The Japan Society of Information and Communication Research, vol. 82, No. 7, pp. 718–724, July 1999).

Figure 10:
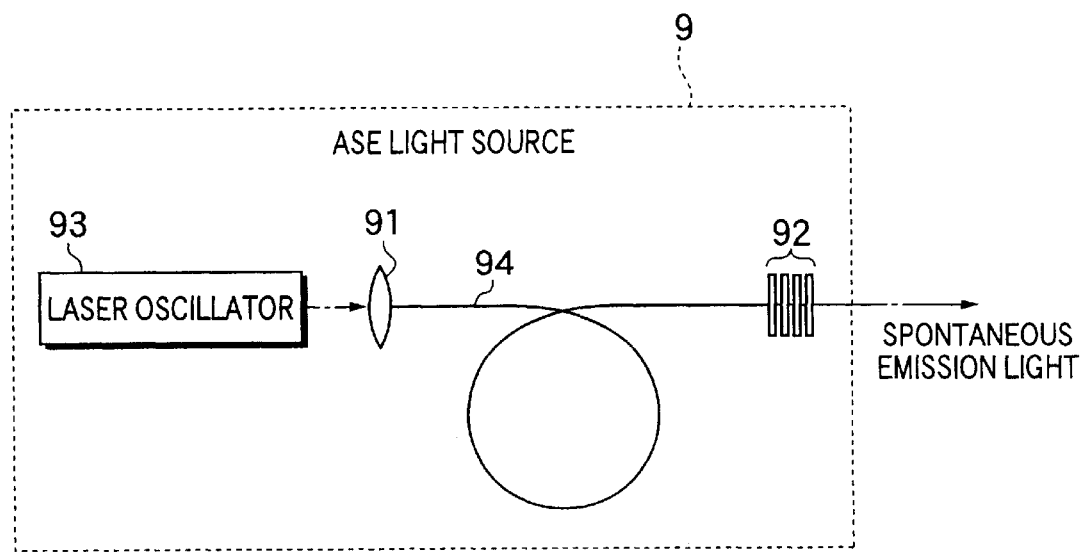
FIG. 10 is a diagram schematically showing an ASE light source used in the sixth embodiment of the present invention.
Figure 11:
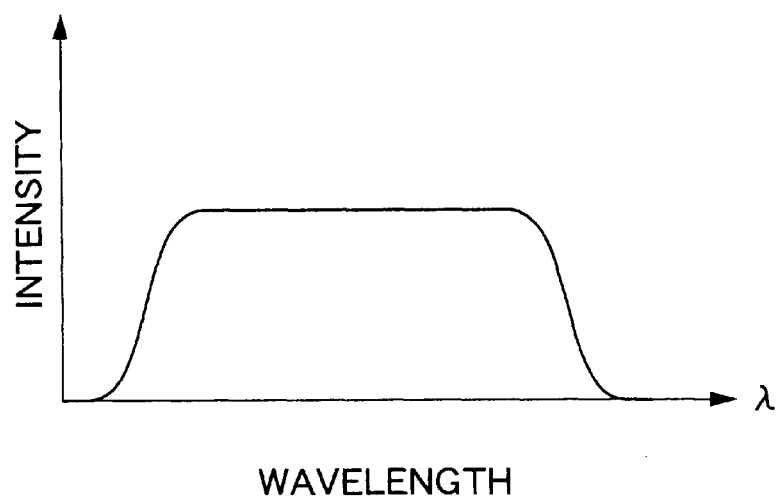
FIG. 11 is a diagram showing a spectrum of a spontaneous emission light emitted from the ASE light source as shown in FIG. 10.

As shown in FIG. 10, the ASE light source 9 includes optical fiber 94 for amplification of the light. This optical fiber 94 comprises first end at which a lens 91 is mounted and second end at which the FBG 92 for reflecting the excitation light is formed. A laser oscillator 93 as an excitation light source is positioned on the left-hand side of the lens 91 in the drawing. The light generated by the laser oscillator 93 allows to be incident upon the optical fiber through the lens 91 and amplified, then a part of the amplifier light is transmitted through the FBG 92 as a spontaneous emission light. The spontaneous emission light emitted from the ASE light source 9 has broad spectrum as shown in FIG. 11. As a broadband light source, a broadband fiber light source may be used instead of the ASE light source.

Referring to FIG. 9 again, the light generated by the ASE light source 9 enters a beam separator 10 which is constructed using a half mirror, an optical circulator, a polarizing beam splitter, or the like. The beam separator 10 transmits the incident light from a first direction toward a second direction, and transmits the reflected light returned from the second direction toward a third direction which is different from the first direction. In the present invention, a half mirror is used as the beam separator 10.

The light emitted from the ASE light source 9 and transmitted through the beam separator 10 is directed onto an optical fiber array 20. The optical fiber array 20 includes fine optical fibers which are arranged in the form of two-dimensional array. It should be noted that a single ASE light source may be provided and assigned to a plurality of optical fibers or a plurality of ASE light sources may be provided and assigned to a plurality of light fibers. Further, the light generated by the single ASE light source may be directed onto the plurality of optical fibers with scanning the light in time series.

Figure 12:
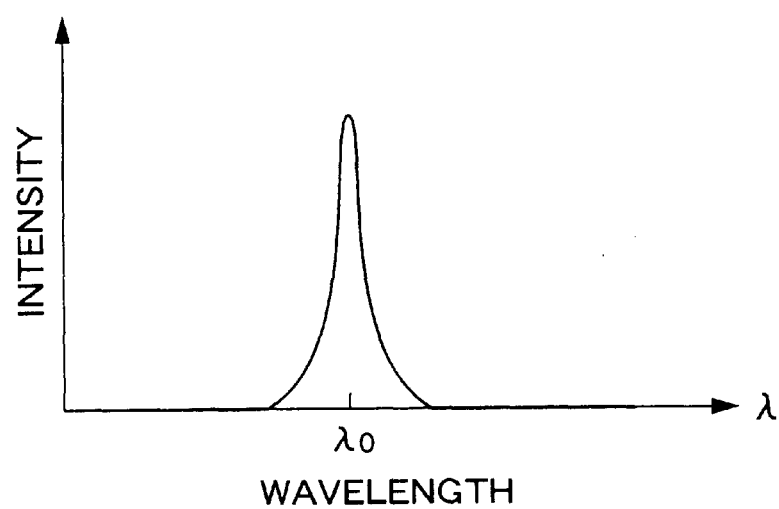
FIG. 12 is a diagram showing a spectrum of light exiting from a narrow-band-pass filter used in the sixth embodiment of the present invention.

The optical fiber array 20 has a narrow-band-pass filter 19 including the FBGs on the tip thereof. The light entering the optical fiber array 20 is reflected by the FBGs of the narrow-band-pass filter 19, and allowed to be incident on the beam separator 10 again. The light generated by the ASE light source 9 is allowed to have the spectrum as shown in FIG. 12 by transmitting through the narrow-band-pass filter 19, and the transmission band thereof is made narrower around the wavelength $\lambda_0$.

The light reflected by the narrow-band-pass filter 19 is allowed to be incident on the beam separator 10 again. The light entering the beam separator 10 is subjected to the change of the traveling path and directed onto the beam separator 12. The light transmitted through the beam separator 12 is allowed to be incident on the optical fiber array 13. The optical fiber array 13 has ultrasonic detecting elements 17 on the tip thereof. The ultrasonic detecting elements 17 include the FBG which are formed on the tips of a plurality of optical fibers, respectively. The light entering the optical fiber array 13 is reflected by the FBGs of the ultrasonic detecting elements 17. The FBGs undergo geometrical displacement by ultrasonic waves applied to the ultrasonic detecting elements 17; thereby the reflected light is modulated and directed onto the beam separator 12 again.

The reflected light entering the beam separator 12 is subjected to the change of the traveling path and directed onto the photodetector 16. The reflected light may be incident upon the photodetector 16 directly or via the optical fibers or the like, or the reflected light may be focussed on the photodetector 16 via an focussing system 15 such as a lens by disposing the focussing system 15 downstream of the beam separator 12. Further, as is the case of the second embodiment, an optical amplifier may be provided which is positioned between the beam separator 12 and the focussing system 15 such as lens or photodetector 16, and serves to amplify the light incident from the beam separator 12 and direct the amplified light onto the focussing system 15 or photodetector 16.

Here, in the FBG, the central wavelength of the reflected light changes at the rate of 0.01 nm/° C. due to temperature variations. Therefore, using a light source which generates single frequency laser beam light causes a problem that the sensitivity of the ultrasonic detecting elements 17 including the FBGs varies considerably due to temperature variations.

However, according to the present embodiment, a certain band near that of a single-frequency laser beam is ensured by narrowing the transmission band of the spontaneous emission light generated by the ASE light source 9 through the use of the narrow-band-pass filter 19, and variations in sensitivity of the ultrasonic receiver due to the temperature variations is reduced.

More specifically, in the present embodiment, the narrow-band-pass filter 19 and the ultrasonic detecting elements 17 are made from the same materials and thermal coupling is provided between the narrow-band-pass filter 19 and the ultrasonic detecting elements 17. The thermal coupling is established, for example, by connecting the narrow-band-pass filter 19 and the ultrasonic detecting elements 17 via a material having a high thermal conductivity, or by placing the narrow-band-pass filter 19 and the ultrasonic detecting elements 17 in physically close proximity to each other. Further, the thermal coupling is also established by placing a heat pipe so as to surround the narrow-band-pass filter 19 and the ultrasonic detecting elements 17. When using a heat pipe, it is necessary to seal therein certain liquid which conducts heat by convection.

AS a result, the temperature of the FBG of the narrow-band-pass filter 19 will be roughly the same as that of the FBG of the ultrasonic detecting element 17, and therefore, even if the reflection property of the ultrasonic detecting elements 17 shifts because of the temperature, the wavelength of the light incident on the ultrasonic detecting elements 17 shifts as well, so that variations in sensitivity of the ultrasonic receiver can be reduced.

Figure 13:
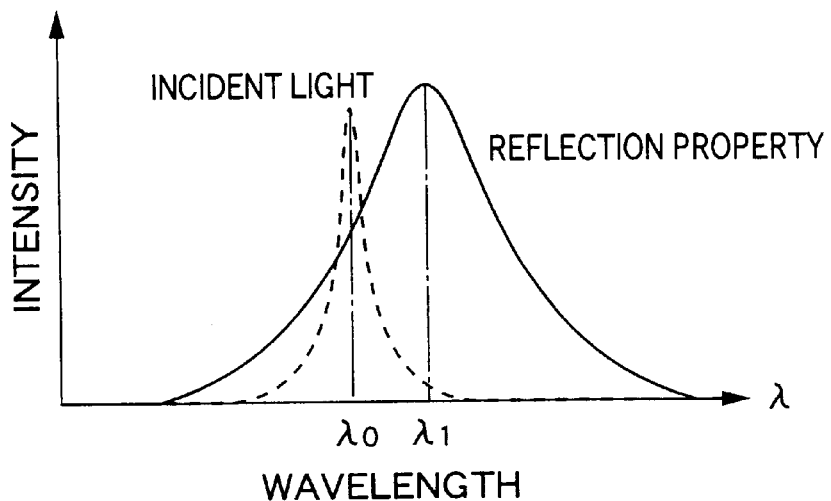
FIG. 13 is a diagram showing a relationship (in the initial state) between the incident light and reflection property of the ultrasonic detecting element in the sixth embodiment of the present invention.
Figure 14:
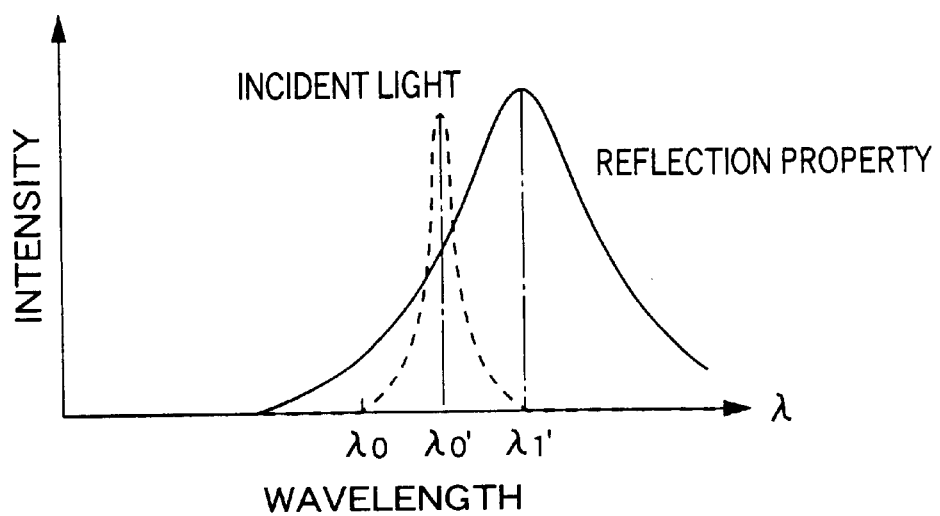
FIG. 14 is a diagram showing a relationship (after the temperature rises) between the incident light and reflection property of the ultrasonic detecting element in the sixth embodiment of the present invention.

As shown in FIG. 13, for example, assume that the central wavelength in the initial state of the light exiting from narrow-band-pass filter 19, i.e. the light incident onto the ultrasonic detecting elements 17, in the initial state is $\lambda_0$, and that the reflection property of the ultrasonic detecting elements 17 is in a state (central wavelength $\lambda_1$) suitable for detecting variations in wavelength of the incident light of a central wavelength $\lambda_0$. Even if the temperature of the ultrasonic detecting elements 17 raises with the passage of the time and thereby the reflection property of the ultrasonic detecting elements 17 changes to the state of central wavelength $\lambda_1'$ as shown in FIG. 14, the central wavelength of the incident lights also changes to $\lambda_0'$, whereby the state suitable for detecting variations in wavelength of the incident light can be sustained. Here, the shift amount of the central wavelength of the ultrasonic detecting elements 17 $(\lambda_1'-\lambda_1)$ is generally equal to the shift amount of the central wavelength of the light emitted from the narrow-band-pass filter 19 $(\lambda_0'-\lambda_0)$.

Next, an ultrasonic receiver according to a seventh embodiment of the present invention will be described below. FIG. 15 is a diagram schematically showing a part of an ultrasonic receiver according to the seventh embodiment of the present invention. An ultrasonic detecting element 18 as shown in FIG. 15 comprises both a Fabry-Perot resonator (FPR) 14 of the first embodiment and a fiber Bragg grating (FBG) 17. That is, the FBG 17 is formed on a tip of the optical fiber 13, and the FPR 14 is formed next to the FBG 17 so as to be nearer the end. As a result, the light not reflected by FBG 17 is allowed to be reflected by FPR 14. The present embodiment is different from the first embodiment in that it is suitable for using with a multi-wavelength laser beam or a wideband laser beam.

Figure 16A:
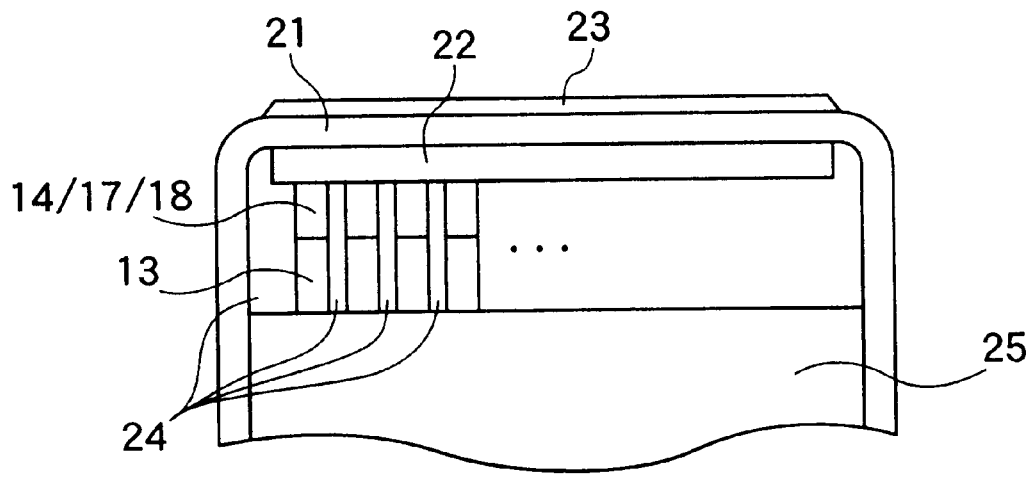
FIGS. 16A to 16C are diagrams showing structure of an ultrasonic probe incorporated in the ultrasonic receiver according to the present invention.
Figure 16B:
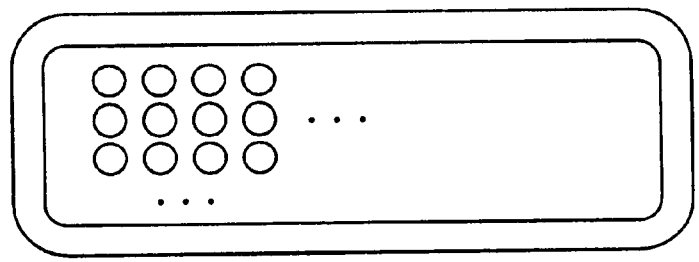
Figure 16C:
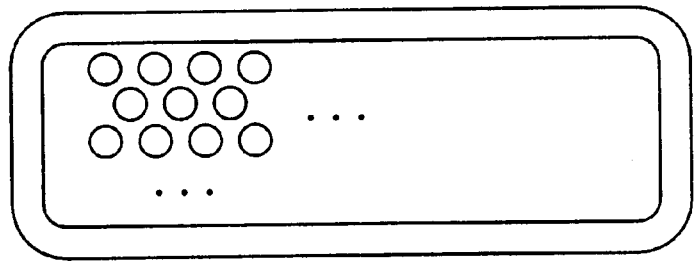

Then, the structure of an ultrasonic probe incorporated in the ultrasonic receivers as mentioned above in connection with some embodiments mentioned above will be described with referring to FIGS. 16A to 16C and FIG. 17. As is shown in FIG. 16A, an optical fiber array 13 provided with ultrasonic detecting elements 14, 17, or 18 is contained in a housing 21. In order to suppress the sidelobe, it is desirable to make the distance between the adjacent ultrasonic detecting elements 14, 17, or 18 less than half of the length of the ultrasonic wave to be received. The ultrasonic detecting elements 14, 17, 18 may be arrayed in a grid pattern so that the elements are positioned at respective apexes of successive squares as shown in FIG. 16B, or may be arrayed in a staggered arrangement so that the elements arranged in respective two adjacent rows or lines are displaced to each other as shown in FIG. 16C in order to increase the density of the ultrasonic detecting elements.

It is desirable to provide an acoustic matching layer 22 between the ultrasonic detecting elements 14, 17, or 18 and the housing 21 in order to match acoustic impedance. The acoustic matching layer 22 may be composed of Pyrex glass, metal-powder-impregnated epoxy resin, etc. which are apt to carry the ultrasonic waves. Further, it is desirable to provide an acoustic lens member 23 including a material such as silicon rubber on the surface of the housing 21 also for protection of the ultrasonic detecting elements. It is also desirable to fill the space between adjacent optical fibers with an acoustic absorbing material 24 to reduce the crosstalk of the ultrasonic waves. Materials suitable for the acoustic absorbing materials 24 are such as metal-powder-impregnated epoxy resin and ferrite-powder-impregnated rubber. The optical fiber array 13 is fixed by resin 25 except for the vicinity of the part where the ultrasonic detecting elements are provided.

Figure 17:
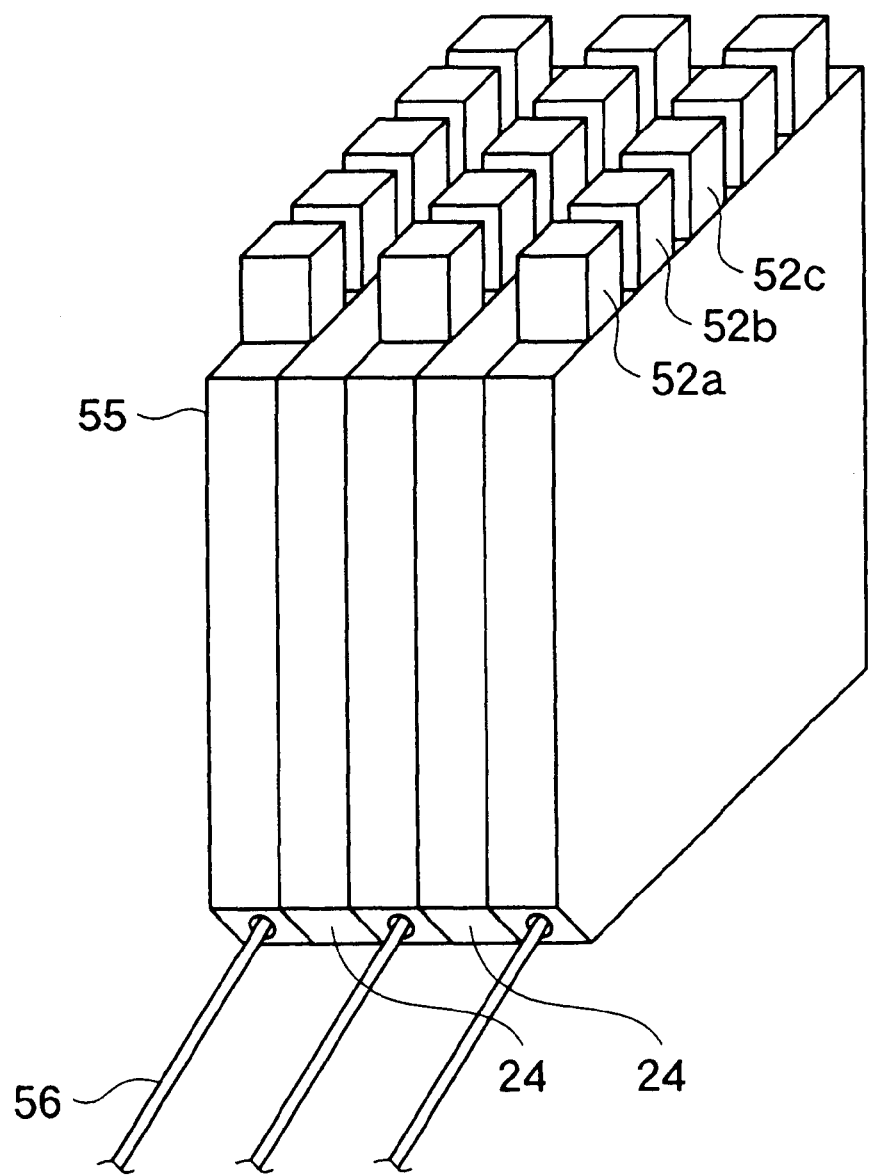
FIG. 17 is a diagram showing structure of an ultrasonic probe incorporated in the ultrasonic receiver according to the present invention.

Further, in order to arrange ultrasonic detecting elements including optical waveguides having Bragg grating structure in a two-dimensional form as shown in FIG. 17, a plurality of substrates 55 in which the optical waveguides are formed may be fixed in parallel. In this case, the plurality of substrates may be arranged so as to put acoustic materials 24 or the like therebetween.

Next, an ultrasonic diagnostic apparatus according to a first embodiment of the present invention will be described with reference to FIG. 18. This ultrasonic diagnostic apparatus is adapted to use the ultrasonic receiver as mentioned above as an ultrasonic detection unit (sensor), and an ultrasonic transmission unit is additionally provided.

Figure 18:
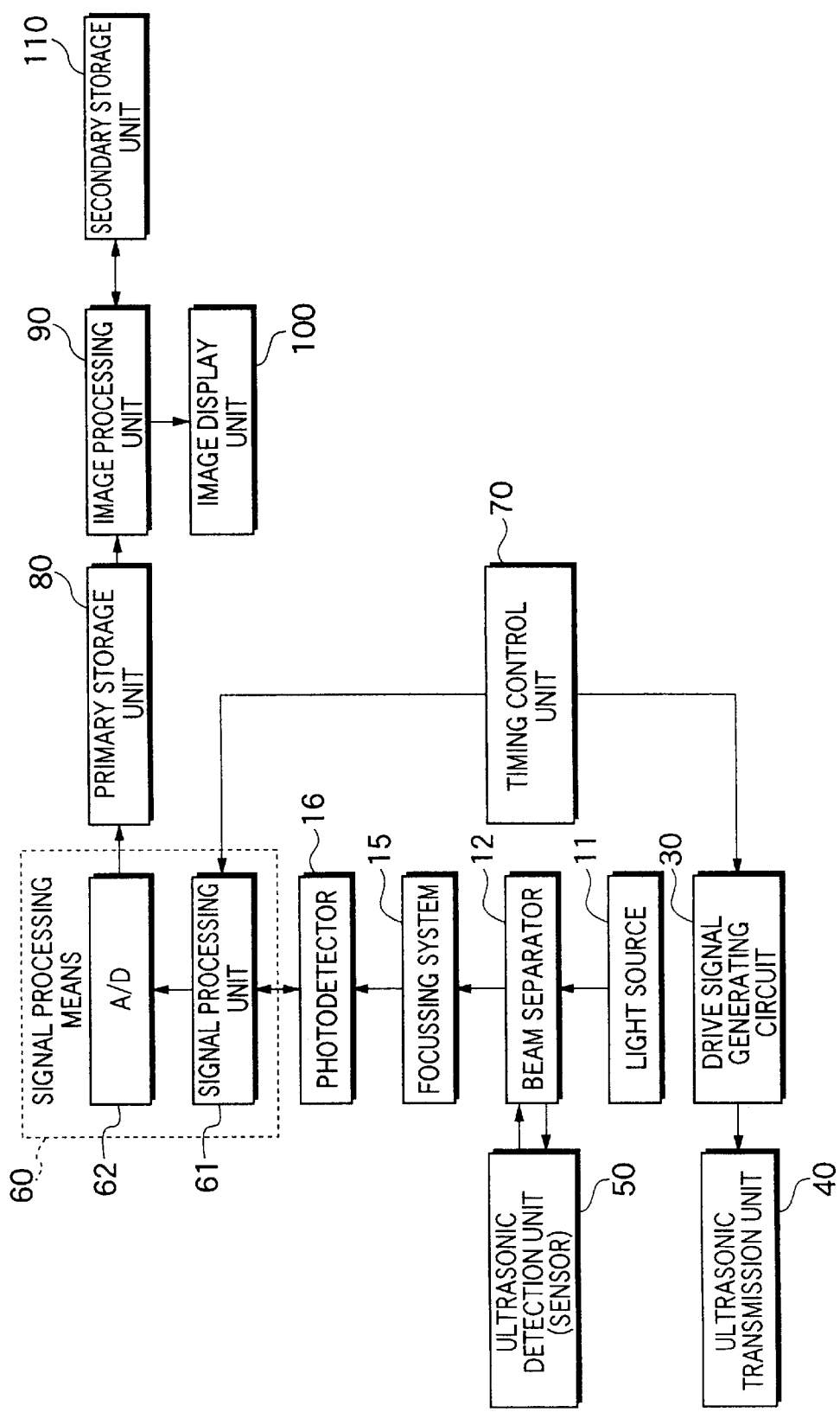
FIG. 18 is a block diagram showing an ultrasonic diagnostic apparatus according to a first embodiment of the present invention.

As shown in FIG. 18, this ultrasonic diagnostic apparatus includes a drive signal generating circuit 30 for generating a drive signal and an ultrasonic transmission unit 40 for transmitting ultrasonic waves in response to this drive signal. The ultrasonic transmission unit 40 includes an oscillator or probe (one dimensional array) each of which has a piezoelectric element such as a PZT or a PVDF. The ultrasonic waves directed onto an object to be inspected is reflected by the object and received by an ultrasonic detection unit (sensor) 50. The sensor 50 incorporates an optical fiber array, an ultrasonic detecting element and soon.

This ultrasonic diagnostic apparatus further comprises a light source 11, a beam separator 12, a focussing system 15 and a photodetector 16 all of which are described above. The detection signal from the photodetector 16 is supplied to a signal processing unit 61 incorporated in signal processing means 60 and converted into a digital signal at an A/D converter 62.

The A/D converter 62 is connected to a primary storage unit 80 in which acquired data of plural planes are stored. An image processing unit 90 reconstructs two-dimensional or three-dimensional data based on the data mentioned above. Those reconstructed data are subjected to processes such as interpolation, response modulation, gradation processing, etc, and then displayed on an image display unit 100. Further, the data processed at the image processing unit 90 are stored in a secondary storage unit 110.

A timing control unit 70 controls a drive signal generating circuit 30 so as to generate drive signals with predetermined timing and also controls the signal processing unit 61 to capture a detection signal supplied from the photodetector 16 after a lapse of a predetermined time from the transmission of the ultrasonic waves. Here, three approaches described below are considered for transmitting ultrasonic waves in the drive signal generating circuit 30 and the ultrasonic transmission unit 40, depending on which a time for capturing certain data and data contents in the signal processing unit 61 will change.

Figure 19:
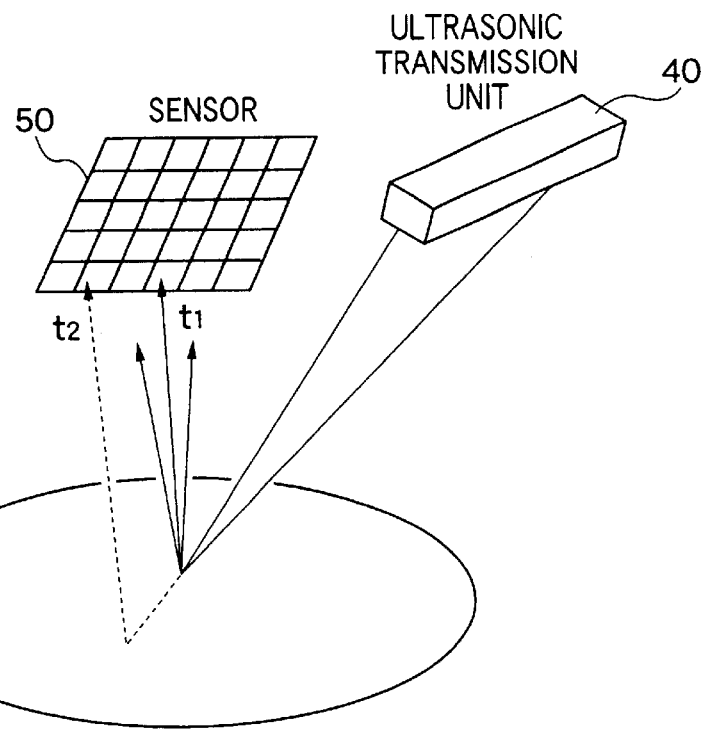
FIG. 19 is a diagram for explaining a detection method in the case where ultrasonic waves are concentrated to have a round section like a pencil beam.

(1) When ultrasonic waves are concentrated like a pencil beam for transmission:

As shown in FIG. 19, by concentrating the transmission waves in a space to have a round section like a pencil beam, scanning an object within a certain plane in the object two-dimensinally, and capturing detection signals by a sensor 50 after a lapse of a predetermined time from the transmission of the ultrasonic waves information on respective points of the certain plane can be obtained. By performing these operations within a section located at a certain depth from the sensor 50, information on the section at the certain depth can be obtained. Thus, a plurality of sectional patterns at different depths can be obtained by repeating these steps at each pencil beam position while changing the capture time. The resultant data are in focus for both transmitting and receiving, and sufficient for displaying as three-dimensional data with no correction.

Figure 20:
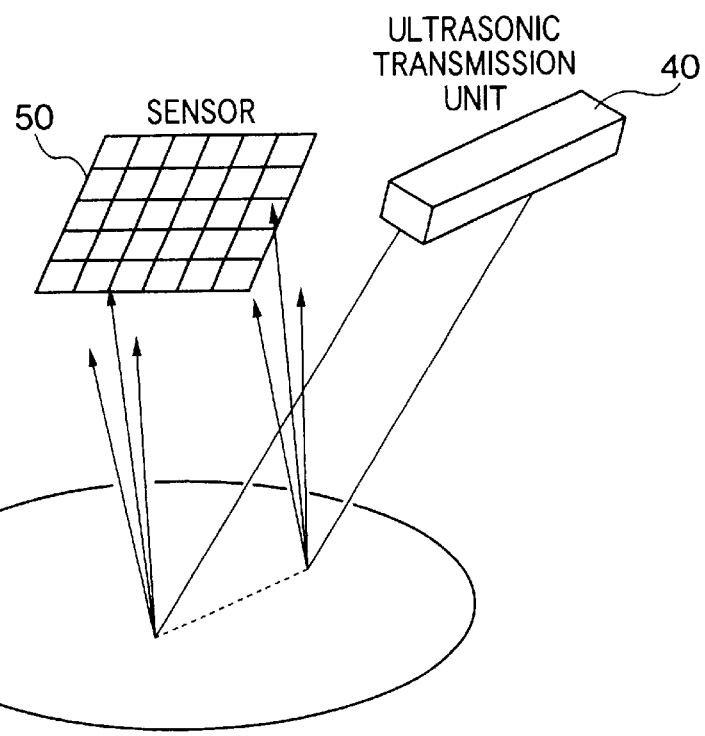
FIG. 20 is a diagram for explaining a detection method in the case where ultrasonic waves are concentrated to have a linear section so that the path thereof form a plane.

(2) When ultrasonic waves are concentrated so as to form a plane:

As shown in FIG. 20, by concentrating the transmission waves emitted from the ultrasonic transmission unit 40 to have a linear section so that the path thereof form a plane by using an acoustic lens, and capturing detection signals by the sensor 50 after a lapse of a predetermined time from the transmission of the ultrasonic waves information on a one-dimensional line at a certain depth can be obtained at once. However, it is inevitable that each point information also contains information on different points within the area to which the ultrasonic waves are applied. Therefore, it is necessary to obtain a display image by reconstructing well-focused data by performing the wavefront synthesis (so-called aperture synthesis) based on the detection signals which are captured in sequence with a time lag.

Figure 21:
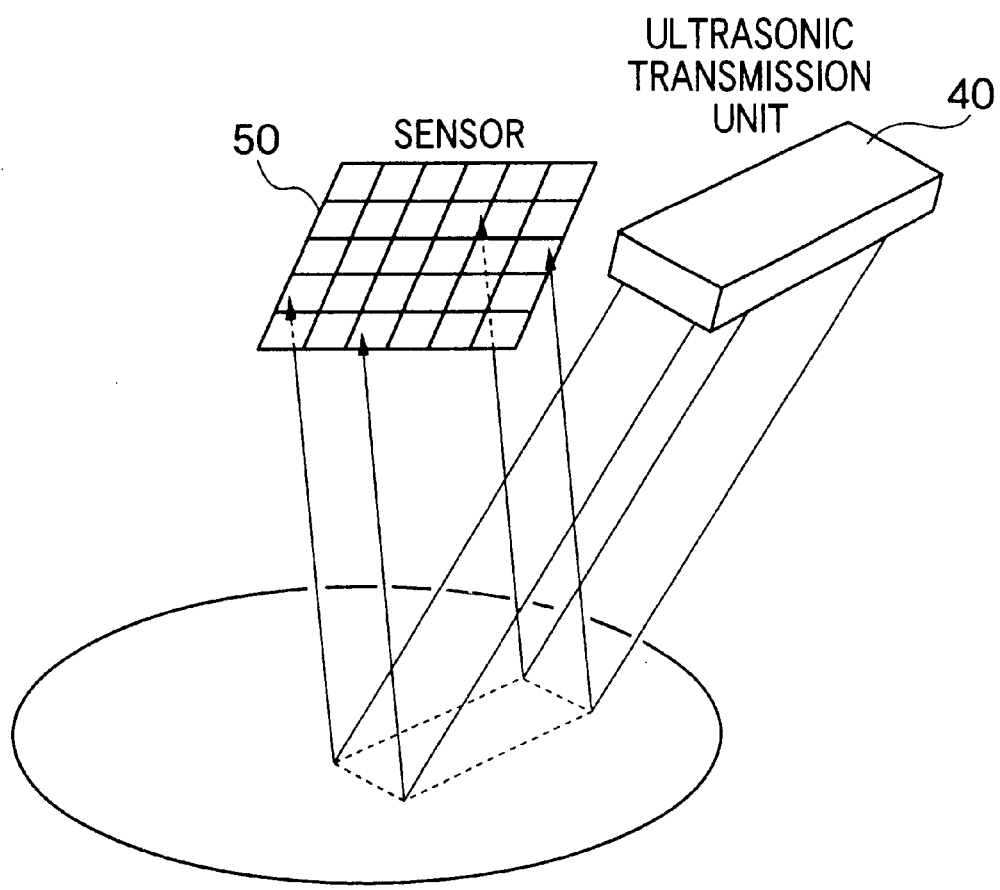
FIG. 21 a diagram for explaining a detection method in the case where ultrasonic waves are transmitted as plane waves.

(3) When ultrasonic waves are transmitted as plane waves:

As shown in FIG. 21, by transmitting the transmission waves as plane waves from the ultrasonic transmission unit 40, and capturing detection signals by the senor 50 after a lapse of a predetermined time from the transmission of the ultrasonic waves information on a two-dimensional plane at a certain depth can be obtained at once. Thus, a plurality of sectional patterns at different depths can be obtained by repeating these steps while changing the capture time. However, it is inevitable that each point information also contains information on different points within the area to which the ultrasonic waves are applied. Therefore, it is necessary to view a display image by reconstructing well-focused data by performing the wavefront synthesis (so called aperture synthesis) based on the detection signals which are captured in sequence with a time lag.

Next, an ultrasonic diagnostic apparatus according to a second embodiment of the present invention will be described below with reference to FIG. 22. In the present embodiment, the ultrasonic detection unit 50 comprising the ultrasonic receiver as mentioned above and the ultrasonic transmission unit 40 are combined with each other for use as an ultrasonic transmitting and receiving unit 120. Except for this, the ultrasonic diagnostic apparatus of the second embodiment is similar to that of the first embodiment.

As described herein above, according to the present invention, light is used for one or two dimensional detection of ultrasonic waves, and thus electric wiring to a large number of microcomponents are not required and increase of crosstalk and electric impedance is prevented. Accordingly, an ultrasonic probe and ultrasonic receiver which are easy to manufacture and provide a good SN ratio, and an ultrasonic diagnostic apparatus incorporating them can be implemented.

What is claimed is:

1. An ultrasonic probe comprising:
   an optical transmission path array including a plurality of optical transmission paths on which light is incident at first ends thereof; and
   a plurality of ultrasonic detecting elements, formed at second ends of said plurality of optical transmission paths, for selectively reflecting light incident through the respective transmission paths, each of said plurality of ultrasonic detecting elements including an ultrasonic sensing part having an optical reflectance which changes in accordance with an applied ultrasonic wave such that a change of the optical reflectance is detected as amplitude modulation of light reflected from said ultrasonic sensing part.

2. An ultrasonic probe according to claim 1, wherein said optical transmission path array includes an optical fiber array including optical fibers.

3. An ultrasonic probe according to claim 2, wherein said optical fibers are single mode fibers.

4. An ultrasonic probe according to claim 1, wherein said optical transmission path array includes optical waveguides formed on a substrate.

5. An ultrasonic probe according to claim 1, wherein each of said plurality of ultrasonic detecting elements has a Fabry-Perot resonator structure.

6. An ultrasonic probe according to claim 1, wherein each of said plurality of ultrasonic detecting elements has a Bragg grating structure.

7. An ultrasonic probe according to claim 1, wherein each of said plurality of ultrasonic detecting elements has both a Fabry-Perot resonator structure and a Bragg grating structure.

8. An ultrasonic probe according to claim 1, wherein said ultrasonic sensing part has a length not larger than ¾ of a wavelength of an ultrasonic wave propagating said ultrasonic sensing part.

9. An ultrasonic probe according to claim 1, further comprising at least one of an acoustic matching layer, an acoustic lens, and an absorbing material.

10. An ultrasonic receiver comprising:
    a plurality of ultrasonic detecting elements, arrayed in a two-dimensional arrangement, for selectively reflecting light, each of said plurality of ultrasonic detecting elements including an ultrasonic sensing part having an optical reflectance which changes in accordance with an applied ultrasonic wave; and
    a photodetector for detecting a change of the optical reflectance as amplitude modulation of light reflected from said ultrasonic sensing part.

11. An ultrasonic receiver according to claim 10, further comprising an optical fiber array containing a plurality of optical fibers each having a first end portion into which light is entered and a second end portion where said ultrasonic detecting element is formed.

12. An ultrasonic receiver according to claim 10, further comprising a plurality of optical waveguide paths formed on a substrate and each having a first end portion into which light is entered and a second end portion where said ultrasonic detecting element is formed.

13. An ultrasonic receiver according to claim 10, further comprising an optical amplifier for amplifying light generated by a light source and supplying the amplified light to said plurality of ultrasonic detecting elements.

14. An ultrasonic receiver according to claim 10, further comprising an optical amplifier for amplifying the light output from said plurality of ultrasonic detecting elements and supplying the amplified light to said photodetector.

15. An ultrasonic receiver according to claim 10, further comprising a light source for generating a single mode laser beam having a wavelength in the range of 500 nm to 1600 nm.

16. An ultrasonic receiver according to claim 10, wherein each of said plurality of ultrasonic detecting elements has a Fabry-Perot resonator structure.

17. An ultrasonic receiver according to claim 10, wherein each of said plurality of ultrasonic detecting elements has a Bragg grating structure.

18. An ultrasonic receiver according to claim 10, further comprising:

a broadband light source for emitting light having a predetermined transmission band; and a narrow-band-pass filter for narrowing the predetermined transmission band of the light emitted from said broadband light source.

19. An ultrasonic receiver according to claim 18, wherein said broadband light source is an ASE (Amplified Spontaneous Emission) light source which emits amplified spontaneous emission light.

20. An ultrasonic receiver according to claim 19, wherein:

said narrow-band-pass filter has a Bragg grating structure made from the same materials as those of the Bragg grating structure of said plurality of ultrasonic detecting elements; and the Bragg grating structure of said narrow-band filter and the Bragg grating structure of said plurality of ultrasonic detecting elements are thermally coupled.

21. An ultrasonic receiver according to claim 10, wherein each of said plurality of ultrasonic detecting elements has both a Fabry-Perot resonator structure and a Bragg grating structure.

22. An ultrasonic receiver according to claim 10, wherein said photodetector includes one of a CCD device and a plurality of photodiodes.

23. An ultrasonic receiver according to claim 10, further comprising at least one of an acoustic matching layer, an acoustic lens, and an absorbing material.

24. An ultrasonic diagnostic apparatus comprising:

a drive signal generating circuit for generating a drive signal;

an ultrasonic transmission unit for transmitting ultrasonic waves to an object in accordance with the drive signal supplied from said drive signal generating circuit;

an ultrasonic detection unit including a plurality of ultrasonic detecting elements for selectively reflecting light, each of said plurality of ultrasonic detecting elements including an ultrasonic sensing part having an optical reflectance which changes in accordance with an applied ultrasonic wave;

a photodetector for detecting a change of the optical reflectance as amplitude modulation of light reflected from said ultrasonic sensing part to generate a detection signal; and signal processing means for processing the detection signal output from said photodetector.

25. An ultrasonic diagnostic apparatus according to claim 24, wherein: said ultrasonic detection unit includes an optical transmission path array including a plurality of optical transmission paths on which light is incident at first ends thereof; and said plurality of ultrasonic detecting elements are formed at second ends of said plurality of optical transmission paths and modulates light incident through the respective optical transmission paths on the basis of an ultrasonic wave reflected from the object.

26. An ultrasonic diagnostic apparatus according to claim 24, wherein said ultrasonic detection unit includes a plurality of ultrasonic detecting elements which are arrayed in a two-dimensional arrangement.

27. An ultrasonic diagnostic apparatus according to claim 24, further comprising an optical amplifier for amplifying light exiting from the light source and supplying the amplified light to the ultrasonic detecting elements.

28. An ultrasonic diagnostic apparatus according to claim 24, further comprising an optical amplifier for amplifying light exiting from said plurality of ultrasonic detecting elements and supplying the amplified light to said photodetector.

29. An ultrasonic diagnostic apparatus according to claim 24, wherein:

each of said plurality of ultrasonic detecting elements has a Bragg grating structure;

said ultrasonic diagnostic apparatus further comprises a narrow-band-pass filter including an ASE (Amplified Spontaneous Emission) light source for emitting amplified spontaneous emission light, and a Bragg grating structure, made from the same materials as those of the Bragg grating structure of said plurality of ultrasonic detecting elements, for narrowing the transmission band of the light emitted from said ASE light source; and the Bragg grating structure of said narrow-band-pass filter and the Bragg grating structure of said plurality of ultrasonic detecting elements are thermally coupled.

30. An ultrasonic diagnostic apparatus according to claim 24, wherein said ultrasonic transmission unit and said ultrasonic detection unit are combined to form an ultrasonic transmitting and receiving unit.

31. An ultrasonic probe for medical diagnosis comprising:

a body, an optical transmission path array within said body, said array comprising a plurality of optical transmission paths, each path having a first end and a second opposite end, said first end being adapted to receive incident laser light; and a plurality of ultrasonic detecting elements, each integrally formed at a respective one of the second ends of said plurality of optical transmission paths, for selectively reflecting light incident through the respective transmission paths, each of said plurality of ultrasonic detecting elements including an ultrasonic sensing part having an optical reflectance which changes in accordance with an applied ultrasonic wave such that a change of the optical reflectance is detected as amplitude modulation of light reflected from said ultrasonic sensing part.

32. An ultrasonic receiver comprising: a plurality of parallel optical transmission paths, each having a first end and a second end, at said first end of each path, incident light being applied thereto and reflected light also exiting therefrom;

an array of a plurality of ultrasonic detecting elements, integrally formed at said second end of each path and operative to selectively reflecting light, each of said plurality of ultrasonic detecting elements including an ultrasonic sensing part having an optical reflectance which changes in accordance with an applied ultrasonic wave; and a photodetector for detecting a change of the optical reflectance as amplitude modulation of light reflected from said ultrasonic sensing part.

33. An ultrasonic receiver according to claim 32, wherein said plurality of paths comprise at least one of an optical fiber and an optical waveguide.

34. An ultrasonic receiver according to claim 32, further comprising an optical amplifier disposed between said first end and said photodetector for amplifying the light output from said plurality of ultrasonic detecting elements and supplying the amplified light to said photodetector.

35. An ultrasonic medical diagnostic apparatus comprising:

a drive signal generating circuit for generating a drive signal for transmission of ultrasonic waves;

an ultrasonic transmission unit for directing ultrasonic waves onto an object in response to the drive signal supplied from said drive signal generating circuit;

an ultrasonic detection unit comprising a source of light, a plurality of ultrasonic detecting elements for selectively reflecting light, each of said plurality of ultrasonic detecting elements including an ultrasonic sensing part having an optical reflectance which changes in accordance with an applied ultrasonic wave;

a photodetector for detecting a change of the optical reflectance as amplitude modulation of light reflected from said ultrasonic sensing part to generate a detection signal; and a signal processor operative to process the detection signal supplied from said photodetector.

36. An ultrasonic medical diagnostic apparatus as set forth in claim 35 further including a timing controller operative to control transmission timing of said drive signal generating circuit and reception timing of said signal processor.

* * * * *